(12) United States Patent
Nichols et al.

(10) Patent No.: US 6,830,758 B2
(45) Date of Patent: Dec. 14, 2004

(54) PSORIASIS PATCH

(75) Inventors: Jane Nichols, Bloomington, MN (US); Teri Buseman, Minnetonka, MN (US); David Rolf, Eden Prairie, MN (US); David Brandwein, New Brighton, MN (US); Daniel M. McWhorter, Eagan, MN (US)

(73) Assignee: Lectec Corporation, Minnetonka, MN (US)

( * ) Notice: Subject to any disclaimer, the term of this patent is extended or adjusted under 35 U.S.C. 154(b) by 128 days.

(21) Appl. No.: 09/824,533

(22) Filed: Apr. 2, 2001

(65) Prior Publication Data

US 2003/0077316 A1 Apr. 24, 2003

(51) Int. Cl.$^7$ .............................. A61K 7/00; A61K 9/70
(52) U.S. Cl. ...................... 424/443; 424/446; 424/448; 424/401
(58) Field of Search ................................ 424/449, 7, 8, 424/401, 403, 394; 514/863

(56) References Cited

U.S. PATENT DOCUMENTS

| | | | |
|---|---|---|---|
| 4,696,854 A | * | 9/1987 | Ethier ......................... 428/287 |
| 5,229,370 A | | 7/1993 | Ammeraal .................... 514/26 |
| 5,376,641 A | | 12/1994 | Ammeraal .................... 514/26 |
| 6,348,212 B2 | * | 2/2002 | Hymes et al. .............. 424/449 |
| 6,495,158 B1 | * | 12/2002 | Buseman et al. ........... 424/443 |

OTHER PUBLICATIONS

*Topical Corticosteroid Therapy, A Novel Approach to Safer Drugs*, Christophers, E., et al., eds; Raven Press, NY (1988), pp. 3–5; ISBN 0881674478.

*Goodman and Gilman's The Pharmacological Basis of Therapeutics*, A. Goodman Gilman et al., eds.; Macmillan, NY, Sixth Edition (1980), pp. 1482–1486; ISBN 0023447206.

"Cyclodextrins–A Unique Form of Starch", (visited Mar. 22, 2001), <http://www.betadexcyclodextrin.com/html/welcome.html>.

"Eczema", Dermatologist.com, (visited on Jan. 4, 2001), <http://www.dermatologist.com/eczema.htm>.

"Eczema/Atopic Dermatitis", *American Academy of Dermatology*, (visited on Jan. 4, 2001), <http://www.aad.org/pamphlets/eczema.html>.

"Guidlines of Care for Contact Dermatitis", *American Academy of Dermatorogy*, (visited on Jan. 4, 2001), <http://www.aad.org/Guidelines/contderm.html>.

"Psoriasis", *American Academy of Dermatology*, (visited Jan. 4, 2001) <http://www.aad.org/pamphlets/Psoriasis.html>.

"Psoriasis Caused Disability That Equals Other Major Medical Diseases", *American Academy of Dermatology*, (visited Jan. 4, 2001) <http://www.aad.org/PressReleases/psoriasis_causes_disability.html>.

"Some Common Dermatoses", *The American Academy of Dermatology*, (visited Jan. 4, 2001), http://www.aad.org.shopping/slides/2.html>.

Gilman, A. G., et al., "Goodman and Gilman's The Pharmacological Basis of Therapeutics", Sixth Edition, pp. 1482–1486.

* cited by examiner

*Primary Examiner*—Gary Kunz
*Assistant Examiner*—Konata M. George
(74) *Attorney, Agent, or Firm*—Schwegman, Lundberg, Woessner & Kluth, P.A.

(57) ABSTRACT

The present invention provides a water insoluble, protective, adhesive skin patch useful for treating or preventing psoriasis, dermatitis, and/or eczema. The adhesive patch includes a backing that is treated with a sizing agent (e.g., a fluorocarbon solution, a silicone-containing compound, or a combination thereof). The present invention also provides a method for treating or preventing at least one of psoriasis, dermatitis, and eczema in a mammal (e.g., human) and a method for exfoliating the skin surface of a mammal.

88 Claims, 6 Drawing Sheets

PSORIASIS PATCH

BACKGROUND OF THE INVENTION

Dermatitis is defined as an inflammation of the skin. Stedman's Medical Dictionary, 25th edition, pp.418–419, Williams & Wilkins, Baltimore. 1990. Among the types of dermatitis are contact dermatitis, atopic dermatitis (i.e., eczema), psoriasis, and seborrheic dermatitis. Stedman's Medical Dictionary, 25th edition, pp.418–419, Williams & Wilkins, Baltimore. 1990.

Contact dermatitis is an altered state of skin reactivity induced by exposure to an external agent. Substances that produce this condition can be an irritant or an allergen. Irritants cause direct tissue damage while allergens induce an immunologic reaction that causes inflammation and tissue damage. With the enormous number of artificial compounds in the human environment today that can be irritants or allergens, contact dermatitis is becoming more common. Over 2800 substances have been identified as contact allergens. Contact dermatitis is responsible for approximately 5.7 million physician visits per year in the U.S.

The term eczema is used to describe all kinds of red, blistering, oozing, scaly, brownish, and itching skin conditions. Examples include seborrheic eczema, nummular eczema, and allergic contact eczema. Eczema is also sometimes used to refer specifically to atopic dermatitis, which is a group of allergic or associated diseases that usually affect several members of a family. These families usually have allergies such as hay fever and asthma. Atopic dermatitis is very common throughout the world. Atopic dermatitis is typically recognized by an itching rash, along with a family history of allergies. It affects about 10% of infants and 3% of the overall U.S. population. The disease can occur at any age, but is most common in infants and young adults. The condition usually improves in childhood or sometime before the age of 25.

In infancy, atopic dermatitis is evidenced by an itching, oozing, and crusting condition that tends to occur mainly on the face and scalp. If the disease continues or occurs beyond infancy, the skin has less of a tendency to be red, blistering, oozing, and crusting. Instead, the lesions become dry, red to brown, and the skin may become scaly and thickened. An intense, almost unbearable itching can continue. Some patients scratch at their skin until it bleeds and crusts, which can lead to infection.

Seborrheic dermatitis is another type of eczema. It consists of a red, scaly, itchy rash in the areas of the body with the highest concentration of sebaceous glands. These include the navel, breasts, underarms, groin, and buttocks.

Psoriasis is a persistent skin disease in which the skin becomes inflamed, producing red, thickened areas with silvery scales, most often on the scalp, elbows, knees, and lower back. The FDA refers to psoriasis as a condition of the scalp or body characterized by irritation, itching, redness, and extreme excess shedding of dead epidermal cells. 21 C.F.R. Chapter 1, Section 358.703 (c). Psoriasis can be so mild that people do not know they have it, or it can be quite severe. The most common form begins with little red bumps that gradually grow larger and form scales. While the top scales flake off easily and often, scales below the surface stick together. When they are removed, the tender, exposed skin bleeds. These small red areas then grow, sometimes becoming quite large. Evidence suggest psoriasis may be caused by malfunctioning white blood cells, causing inflammation in the skin. The cells of the skin then divide too rapidly, causing the skin to shed itself every three to four days. Psoriasis afflicts 2% of the U.S. population and costs the nation between $2 billion and $3 billion each year.

FDA regulations (e.g., 21 C.F.R. Chapter 1, Section 358, Subpart H-Drug Products for the Control of Dandruff, Seborreic Dermatitis and Psoriasis; 21 C.F.R. Ch. 1, Section 348—External Analgesic Drug Products for Over-The-Counter Human Use, Feb. 8, 1983; and 21 C.F.R. Ch. 1, Section 348—External Analgesic Drug Products for Over-The-Counter Human Use, Feb. 27, 1990) regulate what components (i.e., "active ingredients"), in a specified amount, may be described as providing relief or controlling the symptoms of psoriasis, seborrheic dermatitis, or eczema (i.e., contains a topical psoriasis drug, a topical dermatitis drug, or a topical eczema drug). In order to follow FDA regulations, as defined in the over-the-counter (OTC) monograph, only a select number of active ingredients that are able to provide relief or to control the symptoms of psoriasis, dermatitis, or eczema, in a specified amount, may be included in an appropriate dosage form which is described as capable of providing relief or controlling the symptoms of psoriasis, dermatitis, and/or eczema. Consequently, it is difficult to manufacture an adhesive patch that includes a topical psoriasis, dermatitis, or eczema drug, while at the same time (a) maintaining the solubility and stability of the active ingredients in the therapeutic formulation, (b) maintaining the pressure sensitive adhesive properties of the therapeutic formulation such that the patch can effectively exfoliate the skin upon removal, and (c) following FDA regulations.

Several adhesive patches, drug dispensing devices, electrodes, and bandages have been disclosed for applying salicylic acid and/or hydrocortisone to skin. See, e.g., U.S. Pat. Nos. 6,096,334; 6,096,033; 5,741,510; 5,536,263; 4,675,009; 4,307,717; and 4,274,420; which are all commonly assigned to Lec Tec Corporation (Minnetonka, Minn.).

U.S. Pat. No. 4,274,420 discloses an electrode for use in monitoring and stimulation medical applications. The electrode includes a connector plug and a skin-interfacing substrate material. The substrate material can include salicylic acid in 17.8 wt. % (see, Example 2). The reference, however, does not disclose or suggest that the electrode can be used to provide relief or to control the symptoms of psoriasis, seborrheic dermatitis, or eczema. In addition, the reference does not disclose or suggest that salicylic acid can be present in the amount permitted by the FDA (e.g., 1.8 wt. % to 3.0 wt. % of the substrate) to provide relief or to control the symptoms of psoriasis or seborrheic dermatitis. As such, the amount of salicylic acid disclosed therein does not comply with FDA regulations for controlling or treating the conditions of psoriasis or seborrheic dermatitis. See, e.g., 21 C.F.R. Ch. 1, Section 358.710 (b)(4), Apr. 1, 2000 Edition. Additionally, the backing is not disclosed as being treated with a sizing agent. As such, the overall yield of product can be higher, the "holdout" of therapeutic formulation on the backing can be improved, and the degree of penetration of the therapeutic formulation in the backing can be decreased. In addition, the nature and amount of adhesive in the therapeutic formulations that include salicylic acid may not be sufficient to exfoliate the skin, upon removal of the adhesive patch.

U.S. Pat. No. 4,307,717 discloses a bandage that includes a backing element and a substrate attached to the backing element. The substrate includes a matrix that includes a medicament. The medicament can be a keratolytic agent such as salicylic acid (see, col. 3, lines 41–44) or an anti-inflammatory agent such as hydrocortisone (see, col. 3, lines 31–33). However, the amount of salicylic acid or hydrocortisone that can be employed in the matrix or substrate is not disclosed. The reference does not disclose or suggest that the bandage can be used to provide relief or control the symptoms of psoriasis, seborrheic dermatitis, or eczema. In addition, the reference does not disclose or suggest that salicylic acid or hydrocortisone can be present in the amount permitted by the FDA (e.g., 1.8 wt. % to 3.0 wt. % of the substrate for salicylic acid and 0.25 wt. % to 1.0 wt. % of the substrate for hydrocortisone) to provide relief or to control the symptoms of psoriasis, seborrheic dermatitis, or eczema. As such, the amount of salicylic acid and hydrocortisone disclosed therein does not comply with FDA regulations for controlling or treating the conditions of psoriasis, seborrheic dermatitis, or eczema. See, e.g., 21 C.F.R. Ch. 1, Section 358.710 (b)(4), Apr. 1, 2000 Edition and 21 C.F.R. Ch. 1, Section 348.10 (d), Feb. 27, 1990. Additionally, the backing is not disclosed as being treated with a sizing agent. As such, the overall yield of product can be higher, the "holdout" of therapeutic formulation on the backing can be improved, and the degree of penetration of the therapeutic formulation in the backing can be decreased. In addition, the nature and amount of adhesive in the therapeutic formulations that include hydrocortisone may not be sufficient to exfoliate the skin, upon removal of the adhesive patch.

U.S. Pat. No. 4,675,009 discloses a drug dispensing device (e.g., an adhesive skin reservoir) for the transdermal delivery of a medicament. The drug dispensing device includes a backing element and a substrate attached to the backing element. The substrate includes a medicament wherein the medicament can be a keratolytic agent such as salicylic acid (see, col. 3, line 66) or a hormone such as hydrocortisone (see, col. 3, line 63). The salicylic acid can be present in 8–20% of the substrate (see, Example 20). The amount of hydrocortisone that can be employed in substrate is not disclosed. The reference does not disclose or suggest that the drug dispensing device can be used for controlling or treating the conditions of psoriasis, seborrheic dermatitis, or eczema. In addition, the reference does not disclose or suggest that salicylic acid or hydrocortisone can be present in the amount permitted by the FDA (e.g., 1.8 wt. % to 3.0 wt. % of the substrate for salicylic acid and 0.25 wt. % to 1.0 wt. % of the substrate for hydrocortisone) to control or treat the conditions of psoriasis, seborrheic dermatitis, or eczema. As such, the amount of salicylic acid and hydrocortisone disclosed therein does not comply with FDA regulations for controlling or treating the conditions of psoriasis, seborrheic dermatitis, or eczema. See, e.g., 21 C.F.R. Ch. 1, Section 358.710 (b)(4), Apr. 1, 2000 Edition and 21 C.F.R. Ch. 1, Section 348.10 (d), Feb. 27, 1990. Additionally, the backing is not disclosed as being treated with a sizing agent. As such, the overall yield of product can be higher, the "holdout" of therapeutic formulation on the backing can be improved, and the degree of penetration of the therapeutic formulation in the backing can be decreased. In addition, the nature and amount of adhesive in the therapeutic formulations that include hydrocortisone may not be sufficient to exfoliate the skin, upon removal of the adhesive patch.

U.S. Pat. Nos. 5,536,263 and 5,741,510 disclose an adhesive patch for applying medication to the skin. The patch includes a backing and a hydrocolloidal gel located on and in the backing. The gel includes a pressure-sensitive adhesive and a medicament. The medicament can be a keratolytic agent such as salicylic acid (see, U.S. Pat. No. 5,536,263; col. 5; lines 35–36 and U.S. Pat. No. 5,741,510; col. 5, line 35) or an anti-inflammatory agent such as hydrocortisone (see, U.S. Pat. No. 5,536,263; col. 5; lines 30–31 and U.S. Pat. No. 5,741,510; col. 5, lines 30–31). The salicylic acid can be present in 4.1 wt. % (see, U.S. Pat. No. 5,536,263 Example 46 or U.S. Pat. No. 5,741,510 Example 46). The hydrocortisone can be present in 1 wt. % or 0.5 wt. % of the gel (see, Examples 1, 3, 4, 5, 7, and 11 of U.S. Pat. No. 5,536,263 and Examples 1, 2, 3, 4, 5, 7, and 11 of U.S. Pat. No. 5,741,510). The reference does not disclose or suggest that the adhesive patch can be used for controlling or treating the conditions of psoriasis, seborrheic dermatitis, or eczema. In addition, the reference does not disclose or suggest that salicylic acid can be present in the amount permitted by the FDA (e.g., 1.8 wt. % to 3.0 wt. % of the substrate) to control or treat the conditions of psoriasis or seborrheic dermatitis. As such, the amount of salicylic acid disclosed therein does not comply with FDA regulations for controlling or treating the conditions of psoriasis or seborrheic dermatitis. See, e.g., 21 C.F.R. Ch. 1, Section 358.710 (b)(4), Apr. 1, 2000 Edition. The nature and amount of adhesive disclosed therein is not sufficient to exfoliate the skin, upon removal of the adhesive patch. Additionally, the backing is not disclosed as being treated with a sizing agent. As such, the overall yield of product can be higher, the "holdout" of therapeutic formulation on the backing can be improved, and the degree of penetration of the therapeutic formulation in the backing can be decreased. In addition, the nature and amount of adhesive in the therapeutic formulations that include hydrocortisone may not be sufficient to exfoliate the skin, upon removal of the adhesive patch.

U.S. Pat. Nos. 6,096,333 and 6,096,334 disclose adhesive patches for applying medication to the skin. The patch includes a backing layer and a hydrophilic pressure-sensitive adhesive reservoir that includes a medicament. The medicament can be a keratolytic agent such as salicylic acid (see, U.S. Pat. No. 6,096,333; col. 5; line 41 and U.S. Pat. No. 6,096,334; col. 5, line 41) or an anti-inflammatory agent such as hydrocortisone (see, U.S. Pat. No. 6,096,333; col. 5; lines 36–37 and U.S. Pat. No. 6,096,333; col. 5; lines 36–37). The salicylic acid can be present in 4.1 wt. % (see, U.S. Pat. No. 6,096,333 Example 46 and U.S. Pat. No. 6,096,333 Example 46). The hydrocortisone can be present in 1.0 wt. % or 0.5 wt. % (see, Examples 1, 2, 3, 4, 5, 7, 11 of U.S. Pat. No. 6,096,333 and Examples 1, 2, 3, 4, 5, 7, and 11 of U.S. Pat. No. 6,096,334). The references do not disclose or suggest that the adhesive patches can be used for controlling or treating the conditions of psoriasis, seborrheic dermatitis, or eczema. In addition, the reference does not disclose or suggest that salicylic acid can be present in the amount permitted by the FDA (e.g., 1.8 wt. % to 3.0 wt. % of the substrate). As such, the amount of salicylic acid disclosed therein does not comply with FDA regulations for controlling or treating the conditions of psoriasis or seborrheic dermatitis. See, e.g., 21 C.F.R. Ch. 1, Section 358.710 (b)(4), Apr. 1, 2000 Edition. The nature and amount of adhesive disclosed therein may not be sufficient to exfoliate the skin, upon removal of the adhesive patch. Additionally, the backing is not disclosed as being treated with a sizing agent. As such, the overall yield of product can be higher, the "holdout" of therapeutic formulation on the backing can be improved, and the degree of penetration of the therapeutic formulation in the backing can be decreased.

The adhesive patches, drug dispensing devices, electrodes, and bandages disclosed in, e.g., U.S. Pat. Nos. 6,096,334; 6,096,033; 5,741,510; 5,536,263; 4,675,009; 4,307,717; and 4,274,420 have experienced success in applying and/or delivering medication to the skin. There have been manufacturing difficulties, however, with these adhesive patches, drug dispensing devices, electrodes, and bandages. Specifically, it would be economically advantageous to increase the overall yield of these products in the manufacturing processes. It would also be economically beneficial to improve the "holdout" of the therapeutic formulations on the backings. Additionally, it would be economically advantageous to control the degree of penetration of the therapeutic formulations in the backings. Another difficulty with the adhesive patches, drug dispensing devices, electrodes, and bandages disclosed in, e.g., U.S. Pat. Nos. 6,096,334; 6,096,033; 5,741,510; 5,536,263; 4,675,009; 4,307,717; and 4,274,420 is that the nature and amount of adhesive or pressure sensitive adhesive present in the therapeutic formulation does not readily allow for the exfoliation of skin, upon removal of the adhesive patch, drug dispensing device, electrode, or bandage.

There is a need therefore for methods and devices for treating patients with psoriasis, seborrheic dermatitis, or eczema that have minimum adverse effects; have maximum efficacy; are simple and comfortable to use; administers to the skin an effective and current amount of a topical psoriasis, seborrheic dermatitis, or eczema drug; complies with FDA regulations; and/or exfoliates the skin upon removal of the device from the skin. The device will preferably have an overall yield of product that is higher than current devices, will preferably have an improved "holdout" of therapeutic formulation on the backing compared to current devices, and/or will have a lower degree of penetration of the therapeutic formulation in the backing of the device compared to known devices.

SUMMARY OF THE INVENTION

The present invention provides a water insoluble, protective, adhesive skin patch useful for treating or preventing psoriasis, dermatitis, and/or eczema. The adhesive skin patch administers to the skin an effective and known amount of a medicament (i.e., at least one of a topical psoriasis drug, a topical dermatitis drug, and a topical eczema drug). The adhesive skin patch maintains the adhesiveness of the adhesive and the stability of the medicament over a prolonged period of time typically experienced in the manufacturing, packaging, shipping, and/or the storage of the patch.

The medicament, solvent, and pressure sensitive adhesive are positioned on at least a portion of the adhesive patch, in at least a portion of the adhesive skin patch, or on and in at least a portion of the adhesive patch. Preferably, the medicament, solvent, and pressure sensitive adhesive are partially embedded in at least a portion of the adhesive skin patch. Additionally, the adhesive skin patch complies with FDA regulations (e.g., 21 C.F.R. Chapter 1, Subpart H—Drug Products for the Control of Dandruff, Seborrheic Dermatitis, and Psoriasis; 21 C.F.R. Ch. 1, Part 348—External Analgesic Drug Products for Over-The-Counter Human Use, Feb. 8, 1983; and 21 C.F.R. Ch. 1, Part 348—External Analgesic Drug Products for Over-The-Counter Human Use, Feb. 27, 1990).

The adhesive skin patch of the present invention can include a gel that is not water-based. The adhesive skin patch includes a backing that is treated with a sizing agent (e.g., a fluorocarbon solution, a silicone-containing compound, or a combination thereof). The sizing agent can be a hydrophobic sizing agent. The use of such backing prevents immediate wick through and maintains the hydrogel from penetrating the backing too quickly. In addition, the use of such backing provides an adhesive skin patch with a higher yield improvement and superior holdout properties. The use of such backing also obviates the need for a backing liner or a release liner. In such an embodiment, the adhesive skin patch can exist as a self wound adhesive patch.

The present invention provides an adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a sizing agent such that the portion of the backing that is treated with the sizing agent has a surface energy of about 20 dynes/cm$^2$ to about 65 dynes/cm$^2$. The therapeutic formulation includes a medicament selected from one or more topical psoriasis drugs, one or more topical dermatitis drugs, one or more topical eczema drugs, or a combination thereof. The therapeutic formulation includes a solvent that dissolves the medicament and a pressure sensitive adhesive.

The present invention provides another adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a sizing agent such that the portion of the backing that is treated with the sizing agent has a surface energy of about 20 dynes/cm$^2$ to about 65 dynes/cm$^2$. The sizing agent can be a hydrophobic sizing agent. The therapeutic formulation includes salicylic acid or a pharmaceutically acceptable salt thereof present in about 1.8 wt. % to about 3.0 wt. % of the therapeutic formulation, a solvent that dissolves the salicylic acid, and a pressure sensitive adhesive.

The present invention provides another adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a sizing agent such that the portion of the backing that is treated with the sizing agent has a surface energy of about 20 dynes/cm$^2$ to about 65 dynes/cm$^2$. The sizing agent can be a hydrophobic sizing agent. The therapeutic formulation includes a medicament selected from one or more topical psoriasis drugs, one or more topical dermatitis drugs, one or more topical eczema drugs, or a combination thereof; and a hot melt adhesive.

The present invention provides another adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a sizing agent such that the portion of the backing that is treated with the sizing agent has a surface energy of about 20 dynes/cm$^2$ to about 65 dynes/cm$^2$. The sizing agent can be a hydrophobic sizing agent. The therapeutic formulation includes a corticosteroid; a cyclodextrin or a derivative of cyclodextrin that effectively solubilizes the corticosteroid; and a pressure sensitive adhesive.

The therapeutic formulation can be partially embedded in at least a portion of the front side of the backing. The therapeutic formulation can be located on the entire surface of the front side of the backing. The backing can be porous. The backing can be vapor permeable. The backing can include water insoluble material. The backing can have a thickness of about 0.025 mm to about 1.25 mm. The backing can include a nonwoven fabric.

The hydrophobic sizing agent can be a fluorocarbon solution, a Silicone-containing compound, or a combination thereof. The backing that is treated with the fluorocarbon solution can be VILMED™ M1585 W/HY, VILMED™ M1585H/HY, VILMED™ M1586 W/HY, VILMED™ M1586 H/HY, VILMED™ M1570, VILMED™ M1573 F, VILMED™ M1573 FH, VILMED™ M1577 F, VILMED™ M1578 F, VILMED™ M1578 FH, or a combination thereof. The silicone-containing compound can be a polydimethyl siloxane, a dialkylsiloxane, a dimethylsiloxo vinyl alkene, a dialkylsiloxo vinyl alkene, a dimethylsiloxo acrylate, a dialkylsiloxo acrylate, a vinyl terminated polydimethylsiloxane, a vinyl terminated polydialkylsiloxane, or a combination thereof.

The entire front side of the backing can be treated with the sizing agent. The sizing agent can penetrate at least a portion of the underlying surface of the front side of the backing. The sizing agent can be a hydrophobic sizing agent. The sizing agent can penetrate the entire underlying surface of the front side of the backing. The entire backing can be treated with the sizing agent. The backing can include polycellulose fibers, polyester fibers, polyurethane fibers, polyolefin fibers, polyamide fibers, cotton fibers, copolyester fibers, or any mixture thereof. The backing, upon contact with skin, can retain the therapeutic formulation and allow moisture from the skin to pass.

The topical psoriasis drug or the topical dermatitis drug can be coal tar, pyrithione zinc, salicylic acid, selenium sulfide, a pharmaceutically acceptable salt thereof, or any combination thereof. The topical psoriasis drug or the topical dermatitis drug can be salicylic acid, or a pharmaceutically acceptable salt thereof. The salicylic acid, or the pharmaceutically acceptable salt thereof, can be present in about 0.5 wt. % to about 5.0 wt. % of the therapeutic formulation. The salicylic acid, or the pharmaceutically acceptable salt thereof, can be present in about 1.8 wt. % to about 3.0 wt. % of the therapeutic formulation.

The topical eczema drug can be camphor, menthol, benzocaine, butamben picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, hydrocortisone acetate, or a combination thereof. Specifically, the topical eczema drug can be hydrocortisone, hydrocortisone acetate, or a combination thereof, or the topical eczema drug can be lidocaine, lidocaine hydrochloride, or a combination thereof.

The camphor can be present up to about 3.0 wt. % of the therapeutic formulation and menthol can be present up to about 1.0 wt. % of the therapeutic formulation; benzocaine can be present in about 5.0 wt. % to about 20.0 wt. % of the therapeutic formulation; butamben picrate can be present in about 0.5 wt. % to about 1.5 wt. % of the therapeutic formulation; dibucaine can be present in about 0.25 wt. % to about 1.0 wt. % of the therapeutic formulation; dibucaine hydrochloride can be present in about 0.25 wt. % to about 1.0 wt. % of the therapeutic formulation; dimethisoquin hydrochloride can be present in about 0.3 wt. % to about 0.5 wt. % of the therapeutic formulation; dyclonine hydrochloride can be present in about 0.5 wt. % to about 1.0 wt. % of the therapeutic formulation; lidocaine can be present in about 0.5 wt. % to about 4.0 wt. % of the therapeutic formulation; lidocaine hydrochloride can be present in about 0.5 wt. % to about 4.0 wt. % of the therapeutic formulation; pramoxine hydrochloride can be present in about 0.5 wt. % to about 1.0 wt. % of the therapeutic formulation; tetracaine can be present in about 1.0 wt. % to about 2.0 wt. % of the therapeutic formulation; tetracaine hydrochloride can be present in about 1.0 wt. % to about 2.0 wt. % of the therapeutic formulation; benzyl alcohol can be present in about 10.0 wt. % to about 33.0 wt. % of the therapeutic formulation; camphor can be present in about 0.1 wt. % to about 3.0 wt. % of the therapeutic formulation; juniper tar can be present in about 1.0 wt. % to about 5.0 wt. % of the therapeutic formulation; phenolate sodium can be present in about 0.5 wt. % to about 1.5 wt. % of the therapeutic formulation; resorcinol can be present in about 0.5 wt. % to about 3.0 wt. % of the therapeutic formulation; diphenhydramine hydrochloride can be present in about 1.0 wt. % to about 2.0 wt. % of the therapeutic formulation; tripelennamine hydrochloride can be present in about 0.5 wt. % to about 2.0 wt. % of the therapeutic formulation; hydrocortisone can be present in about 0.25 wt. % to about 1.0 wt. % of the therapeutic formulation; corticosteroid can be present in about 0.25 to about 5.0 wt. % of the therapeutic formulation; camphor can be present in about 3 wt. % to about 10.8 wt. % of the therapeutic formulation with phenol; camphor can be present in about 3 wt. % to about 10.8 wt. % of the therapeutic formulation with metacresol present in about 1 wt. % to about 3.6 wt. % of the therapeutic formulation, as camphorated metacresol; or hydrocortisone acetate can be present in about 0.25 wt. % to about 1.0 wt. % of the therapeutic formulation.

The medicament (i.e., the topical psoriasis drug, the topical dermatitis drug, the topical eczema drug, or a combination thereof) can be a corticosteroid. The corticosteroid can be at least one of cortisol (hydrocortisone); tetrahydrocortisol; prednisone (cortisone); prednisolone (cortisol); 6α-methylprednisolone; fludrocortisone (9α-fluorocortisol); 11-desoxycortisol; cortisone (11-dehydrocortisol); corticosterone; triamcinolone (9α-fluoro-16α-hydroxyprednisolone); paramethasone (6α-fluoro-16α-methylprednisolone); betamethasone (9α-fluoro-16β-methylprednisolone); dexamethasone (9α-fluoro-16α-methylprednisolone); desoxycorticosterone acetate (doca acetate, percorten acetate); desoxycorticosterone pivalate (percorten pivalate); fludrocortisone acetate (florine acetate); cortisol (hydrocortisone) (cortef, hydrocortone); cortisol acetate (cortef acetate, hydrocortone acetate); cortisol cypionate (cortef); cortisol sodium phosphate (hydrocortone phosphate); cortisol sodium succinate (solu-cortef); beclopmethasone dipropionate (vanceril); betamethasone (celestone); betamethasone sodium phosphate and acetate (celestone soluspan); betamethasone dipropionate (diprosone); betamethasone valerate (valisone); betamethasone benzoate (benisone, flurodate); cortisone acetate (cortone acetate); dexamethasone (decadron, gammacorten); dexamethasone sodium phosphate (decadron phosphate, hexadrol phosphate); dexamethasone acetate (decadron-L.A.); fuprednisolone (alphadrol); meprednisone (betapar); methylprednisolone (medrol); methylprednisolone acetate (depo-medrol, medrol acetate); methylprednisolone sodium succinate (solu-medrol); paramethasone acetate (haldrone); prednisolone (delta-cortef); prednisolone acetate (meticortelone acetate); prednisolone sodium phosphate (hydeltrasol); prednisolone sodium succinate (meticortelone soluble); prednisolone tebutate (hydelta-T.B.A.); prednisone (deltasone, paracort); triamcinolone (aristocort, kenacort); triamcinolone acetonide (aristoderm, kenalog); triamcinolone diacetate (aristocort diacetate, kienacort diacetate); triamcinolone hexacotonide (aristospan); desonide (tridesilon); desoximetasone (topicort); flumethasone pivalate (locorten); fluocinolone acetonide (fluonid, synalar); fluocinonide (lidex, topsyn); fluorometholone (oxylone); flurandrenolide (cordran); halcinonide (halog); medrysone (HMS liquifilm, medrocort); aclometasone dipropionate (alclovate); betamethasone-17-benzoate (benisone, flurobate); betamethasone dipropionate (diprosone); betamethasone-17-valerate (valisone); clobetasol propionate (temovate); desonide (desowen, tridesilon); dexamethasone (aeroseb-D); desoximetasone (topicort); diflorasone diacetate (florone); flumethasone pivalate (locorten); fluocinolone acetonide (synalar, synalar-HP, neosynalar, fluonid); fluocinolone acetonide acetate (lidex; lidex-E; topsyn); fluorometholone (oxylone); flurandrenolide (cordran); halcinonide (halog); hydrocortisone (cort-dome, lubricort); hydrocortisone acetate (cortef, carmol HC, neo-cortef); hydrocortisone-17-valerate (westcort); prednisolone (metiderm); triamcinolone acetonide (kenalog, orabase, kenalog-S, mycolog, aristocort, aristocort-A, aristoderm, neo-aristoderm, neo-aristocort); temovate; diprolen; psorcon; temovate; diprolene; cyclocort; diprosone; florone; halog; lidex; maxiflor; topicort; aristocort A; diprosone; florone; maxiflor; valisone; cordran; kenalog; synalar; topicort LP; westcort; cordran; diprosone; kenalog; locold; synalar; valisone; westcort; aclovate; desowen; locorten; synalar; tridesilone; valisone; hydrocortisone; dexamethasone; flumethalone; prednisolone; methylprednisolone; augmented betamethasone dipropionate (diprolene); diflorasone diacetate (psorcon); clobetasol propionate (temovate); halobetasol propionate (ultravate); amcinonide (cyclocort); betamethasone dipropionate (diprolene, diprosone); diflorasone diacetate (florone); halcinonide (halog); fluocinonide (lidex); diflorasone diacetate (maxiflor); betamethasone dipropionate (maxivate); diflorasone diacetate (psorcom); desoximetasone (topicort); (aristocort A); amcinonide (cyclocort); betamethasone dipropionate (diprosone); mometasone furoate (elocon); diflorasone diacetate (florone); halcinonide (halog); fluocinonide (lidex-E); diflorasone diacetate (maxiflor); betamethasone dipropionate (maxivate, psorion); betamethasone valerate (valisone); flurandrenolide (cordran); fluticasone propionate (cutivate); mometasone furoate (elocon); triamcinolone acetonide (kenalog); fluocinolone acetonide (synalar); hydrocortisone valerate (westcort); flurandrenolide (cordran); fluticasone propionate (cutivate); betamethasone dipropionate (diprosone); triamcinolone acetonide (kenalog); hydrocortisone butyrate (locoid); fluocinolone acetonide (synalar); betamethasone valerate (valisone); hydrocortisone valerate (westcort); alclometasone dipropionate (aclovate); triamcinolone acetonide (aristocort); desonide (desowen); flumethasone pivalate (locorten); fluocinolone acetonide (synalar); desonide (tridesilon); betamethasone valerate (valisone); hydrocortisone (eldecort, dexamethasone, flumethalone, hydrocortisone, methylprednisolone, or prednisolone); betamethasone; and dexamethasone. The corticosteroid can be present up to about 5 wt. % of the therapeutic formulation.

The therapeutic formulation can include a complexing agent that effectively solubilizes or stabilizes the medicament. The complexing agent can be a cyclodextrin, or a derivative of cyclodextrin. The cyclodextrin or the derivative of cyclodextrin can be alpha-cyclodextrin, beta-cyclodextrin, gamma-cyclodextrin, alpha-cyclodextrin sulfate, beta-cyclodextrin sulfate, gamma-cyclodextrin sulfate, alpha-hydroxypropyl cyclodextrin, beta-hydroxypropyl cyclodextrin, gamma-hydroxypropyl cyclodextrin, alpha-cyclodextrin phosphate, beta-cyclodextrin phosphate, or gamma-cyclodextrin phosphate.

The solvent can include a polyhydric alcohol, water, or a combination thereof. The polyhydric alcohol can be propylene glycol, ethylene glycol, triethylene glycol, or a combination thereof. Alternatively, the solvent can include water; triethylene glycol; glycerin; propylene glycol; triacetin; 1,3-propane diol; 2-methyl-1,3-propane diol; glycerol ricinoleate; PEG-6 caprylic/capric glycerides; caprylic/capric triglycerides; propyleneglycol dicaprylate/dicaprate; glycerol monostearate; glycerol monocaprylate; glycerol monolaurate; neopentyl alcohol; 1-hexadecanol; hydroxypropyl beta-cyclodextrin; vitamin E; vitamin E acetate; deoxycholic acid; taurodeoxycholic acid; 3-[(3-cholamidopropyl)dimethylammonio]-1-propane-sulfonate; BigCHAP; cholic acid; cholesterol NF; propylene carbonate; lecithin; a pharmaceutically acceptable salt thereof; or a combination thereof. The solvent can be present in about 3.0 wt % to about 25.0 wt. % of the therapeutic formulation. Specifically, the propylene glycol can be present in about 3.0 wt. % to about 30.0 wt. % of the therapeutic formulation; the water can be present in about 2.0 wt. % to about 20.0 wt. % of the therapeutic formulation; and/or the triethylene glycol can be present in about 2.0 wt. % to about 30.0 wt. % of the therapeutic formulation. More specifically, the propylene glycol can be present in about 3.0 wt. % to about 11.0 wt. % of the therapeutic formulation; the water can be present in about 2.0 wt. % to about 20.0 wt. % of the therapeutic formulation; and/or the triethylene glycol can be present in about 2.0 wt. % to about 20.0 wt. % of the therapeutic formulation.

The therapeutic formulation can further include a filler. The filler can be malto dextrin. The malto dextrin can be present in about 1.0 wt. % to about 10.0 wt. % of the therapeutic formulation.

The pressure sensitive adhesive can include one or more acrylic ester copolymers. Each of the one or more acrylic ester copolymers can be present up to about 20.0 wt. % of the therapeutic formulation. All of the one or more acrylic ester copolymers, combined, can be present in about 5.0 wt. % to about 30.0 wt. % of the therapeutic formulation. The pressure sensitive adhesive can be located on the entire portion of surface of the front side of the backing. The pressure sensitive adhesive can be at least partially embedded in the front side of the backing. The pressure sensitive adhesive can be completely embedded in the backing.

The pressure sensitive adhesive can further include glycerin. The glycerin can be present in about 25.0 wt. % to about 70.0 wt. % of the therapeutic formulation. The glycerin can be present in about 40.0 wt. % to about 55.0 wt. % of the therapeutic formulation.

The pressure sensitive adhesive can include an emulsifier. The emulsifier can be pectin. The pectin can be present in about 2.0 wt. % to about 10.0 wt. % of the therapeutic formulation.

The pressure sensitive adhesive can include one or more compounds that provide structure and strength to the pressure sensitive adhesive or provide structure and strength to the therapeutic formulation. The compound that provides structure and strength to the pressure sensitive adhesive or provide structure and strength to the therapeutic formulation can be karaya, a polyacrylamide, xanthum gum, guar gum, a natural polymer, a synthetic polymer, a hydrophilic polymer, a hydrocolloidal polymer, starch, a starch derivative, vinyl acetate copolymer, polyvinyl pyrrolidone, polyethylene oxide, algin, derivatives of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS or a mixture thereof. The compound that provides structure and strength to the pressure sensitive adhesive or provide structure and strength to the therapeutic formulation can be polyacrylamide. The compound that provides structure and strength to the pressure sensitive adhesive or provide structure and strength to the therapeutic formulation can be karaya. The compound that provides structure and strength to the pressure sensitive adhesive or provide structure and strength to the therapeutic formulation can be a combination of polyacrylamide and karaya. The polyacrylamide can be present in about 8.0 wt. % to about 30.0 wt. % of the therapeutic formulation. The karaya can be present in about 8.0 wt. % to about 40.0 wt. % of the therapeutic formulation.

The therapeutic formulation can further include one or more skin conditioners. The skin conditioner can be calamine, aloe, lanolin, glycerin, Vitamin E, Vitamin E acetate, farnesol, glycyrrhetinic acid, or a combination thereof. The aloe can be present up to about 2.0 wt. % of the therapeutic formulation. The Vitamin E acetate can be present up to about 2.0 wt. % of the therapeutic formulation.

The therapeutic formulation can further include one or more antimicrobial agents. The antimicrobial agent can be a β-lactam compound, an aminoglycoside, or an antifungal agent. The antimicrobial agent can be erythromycin, tetracycline, clindamycin, or cephalosporin. The therapeutic formulation can further include an antiseptic agent. The antiseptic agent can be triclosan, phenoxy isopropanol, chlorhexidine gluconate, povidone iodine, or any combination thereof.

The therapeutic formulation can further include one or more preservatives. The preservative can be quat 15, methyl paraben, ascorbic acid, or a combination thereof. The preservative can be present up to about 10.0 wt. % of the therapeutic formulation.

The adhesive patch can have a thickness of about 0.20 mm to about 0.75 mm. The adhesive patch can further include a release liner that is mounted on the front side of the backing. More than one patch can be mounted on the release liner. For example, about 2 to about 20 adhesive patches can be mounted on the release liner. The adhesive patch can be crescent, circular, or oval. The circular adhesive patch can have a diameter of about 0.1 inch to about 1.0 inch.

The present invention also provides a method for treating or preventing at least one of psoriasis, dermatitis, and eczema in a mammal (e.g., human). The method includes applying to the skin surface of the mammal having the psoriasis, dermatitis, and/or eczema, or the skin surface of the mammal at risk thereof an adhesive patch of the present invention for a period of time effective to treat or prevent psoriasis, dermatitis, and/or eczema. The skin surface of the mammal having the psoriasis, dermatitis, and/or eczema or the skin surface of the mammal at risk thereof can include the head, face, scalp, neck, shoulder, chest, back, arm, hand, leg, foot, navel, breast, underarm, groin, buttock, elbow, knee, eyelid, outer surface of the ear, gluteal fold, or any combination thereof. The period of time that the adhesive patch is applied to the skin surface can be about one hour to about 12 hours.

The present invention also provides a method for exfoliating the skin surface of a mammal (e.g., human). The method includes applying to the skin surface of the mammal in need of such exfoliation an adhesive patch of the present invention and removing the adhesive patch, thereby effectively exfoliating the skin surface. The adhesive patch can be applied to the skin surface of the mammal for about one second to about 12 hours. In addition, the skin surface in need of such exfoliation can include the head, face, scalp, neck, shoulder, chest, back, arm, hand, leg, foot, navel, breast, underarm, groin, buttock, elbow, knee, eyelid, outer surface of the ear, gluteal fold, or any combination thereof.

DETAILED DESCRIPTION OF THE INVENTION

Figure 1:
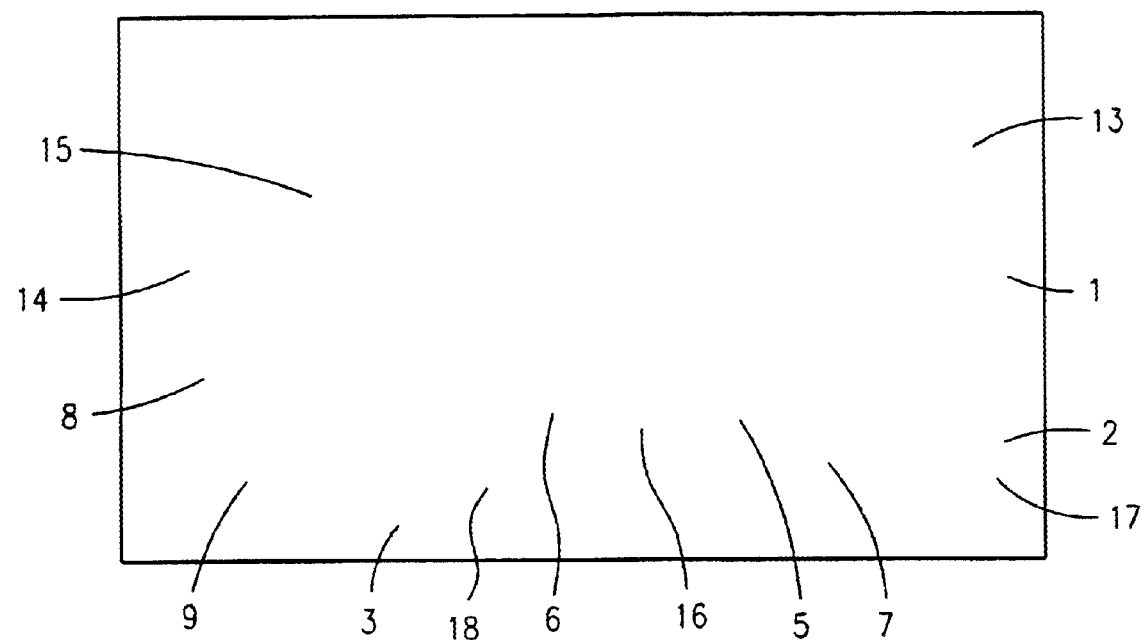
FIG. 1 illustrates the front side of an adhesive patch of the present invention.
Figure 2:
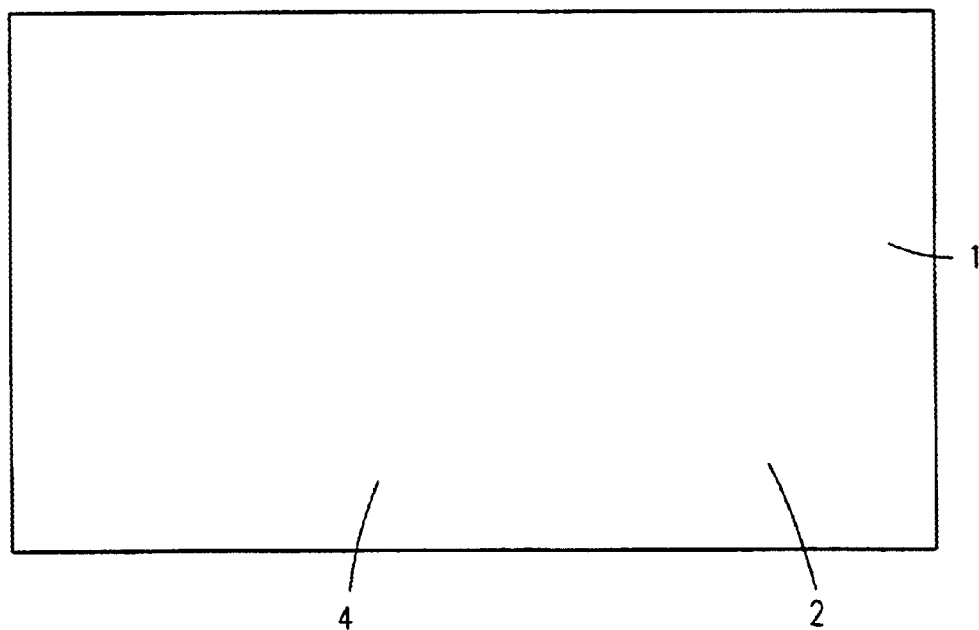
FIG. 2 illustrates the back side of an adhesive patch of the present invention.
Figure 3:
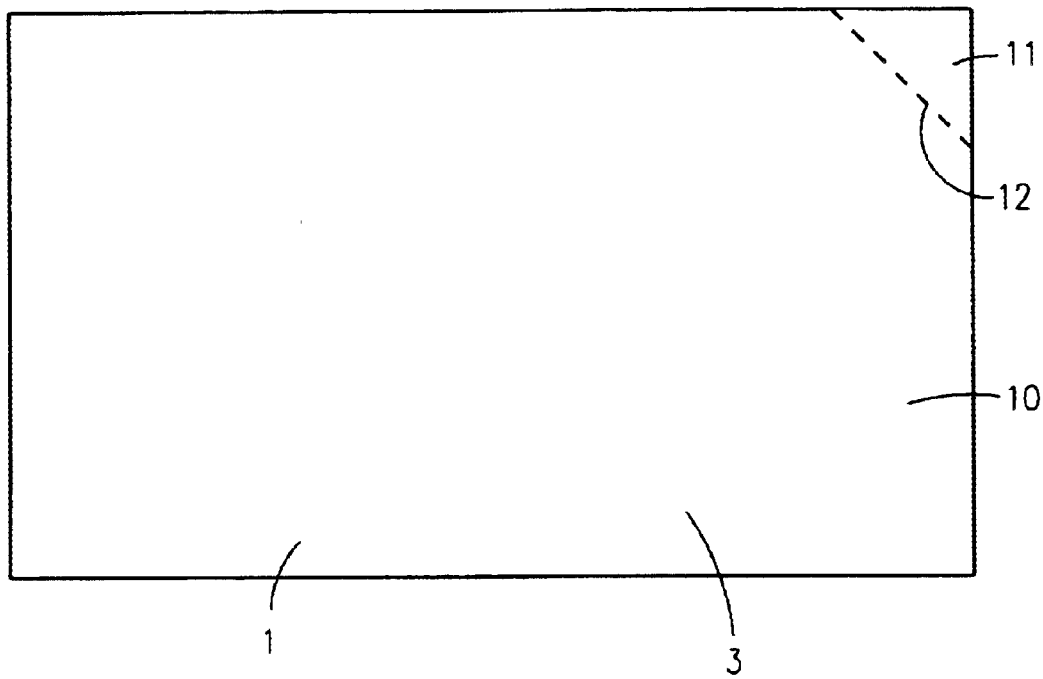
FIG. 3 illustrates the front side of an adhesive patch of the present invention with a release liner attached to the patch.
Figure 4:
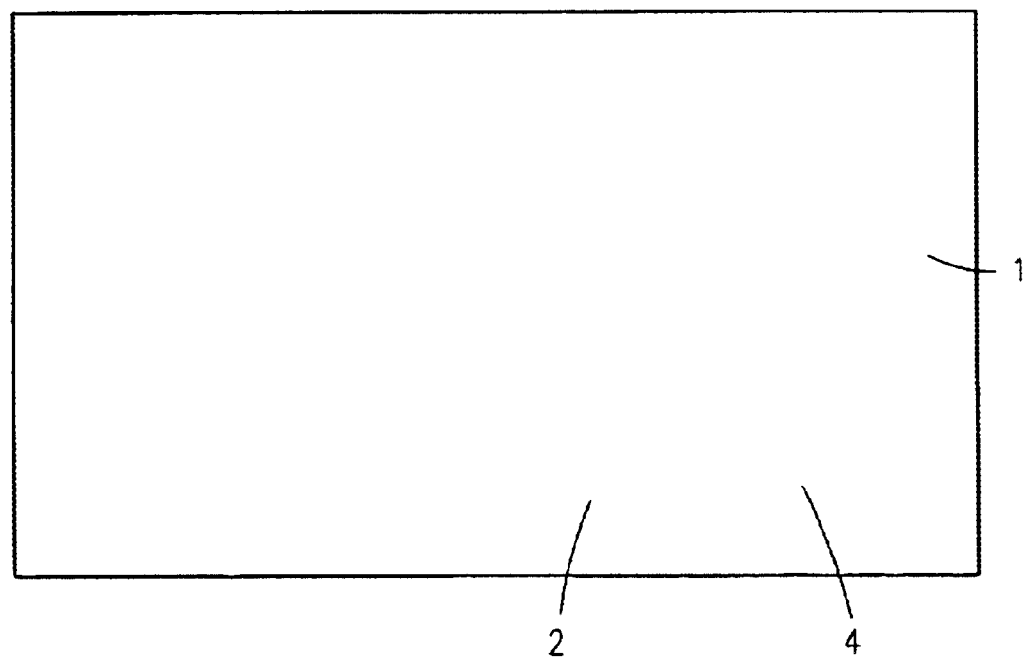
FIG. 4 illustrates the back side of an adhesive patch with a release liner attached to the patch.
Figure 5:
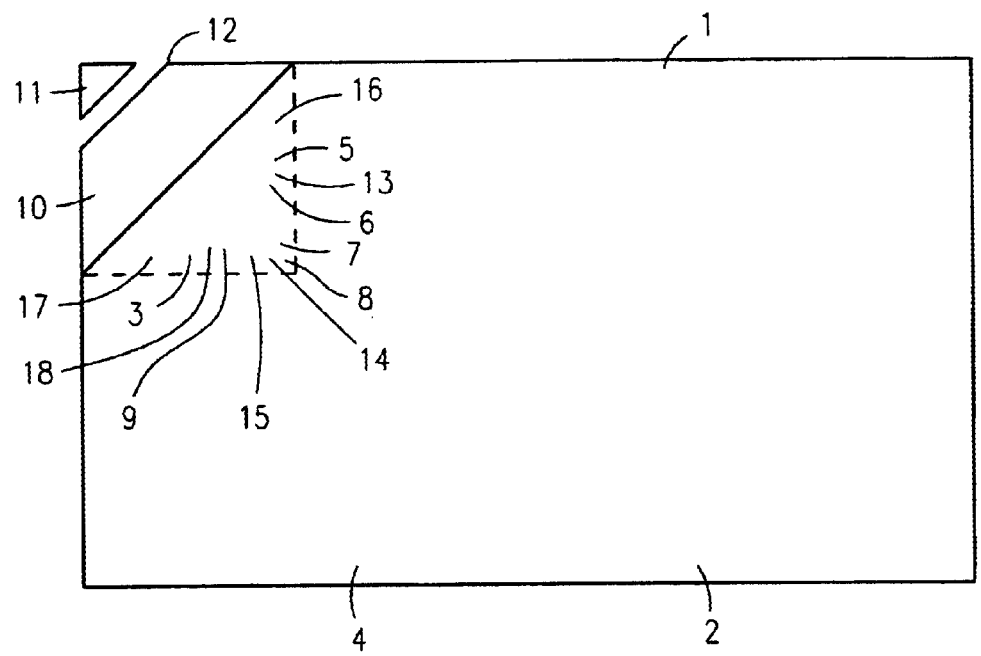
FIG. 5 illustrates the back side of an adhesive patch of the present invention with a release liner attached to the patch, wherein the patch is partially detached from the release liner.
Figure 6:
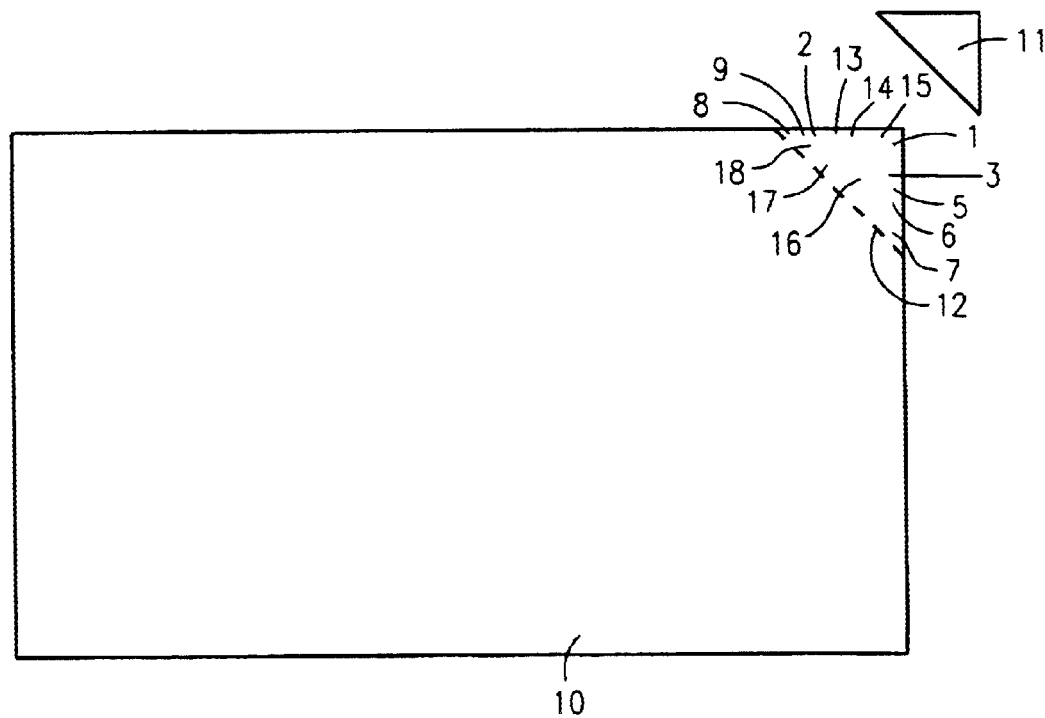
FIG. 6 illustrates the back side of an adhesive patch of the present invention with a release liner attached to the patch, wherein the patch is partially detached from the release liner.

The present invention provides a unique adhesive vehicle. The vehicle has pressure sensitive adhesive qualities due to its composition and viscoelastic nature. The adhesive is hydrophilic and therefore water can dissolve into or evaporate from the adhesive, depending on the conditions to which it is exposed. This water exchange capability implies that if the adhesive is on a suitably porous backing and is applied to the skin, it will not be occlusive as most drug delivery patches are. The occlusive nature of conventional drug delivery patches is thought to play an important role in enhancing drug absorption, but also often results in greater incidence of skin irritation. The relatively low occlusiveness of the present invention can be envisioned to be a special adhesive ointment or gel which is water-breathable, such as a water washable or water soluble ointment or gel.

The present invention provides an ointment or gel on a backing. The ointment or gel includes an effective, known, and safe amount of a medicament that is useful for treating or preventing psoriasis, dermatitis, and/or eczema; and a pressure sensitive adhesive. The backing is pliable and/or stretchable. Since the backing can be porous and/or vapor permeable, many consumers typically refer to the device as a "patch," a "skin patch," or an "adhesive skin patch." As such, the device (i.e., the ointment or gel on the backing) will herein be referred to as a patch, a skin patch, an adhesive skin patch and/or as a psoriasis patch. It is appreciated that those skilled in the art understand that the term "patch" is used to refer to the device and is not otherwise limiting in any manner.

The present invention provides a water insoluble, protective, adhesive patch useful for treating or preventing psoriasis, dermatitis, and/or eczema. The patch administers to the skin an effective and known amount of a medicament. The patch maintains the adhesiveness of the adhesive and the stability of the medicament over a prolonged period of time typically experienced in the manufacturing, packaging, shipping, and/or the storage of the patch. The patch complies with FDA regulations (e.g., 21 C.F.R. Chapter 1, Subpart H—Drug Products for the Control of Dandruff, Seborrheic Dermatitis, and Psoriasis; 21 C.F.R. Ch. 1, Part 348— External Analgesic Drug Products for Over-The-Counter Human Use, Feb. 8, 1983; and 21 C.F.R. Ch. 1, Part 348—External Analgesic Drug Products for Over-The-Counter Human Use, Feb. 27, 1990). The adhesive patch of the present invention can include a gel that is not water-based. The adhesive patch includes a backing that is treated with a sizing agent (e.g., a fluorocarbon solution, a silicone-containing compound, or a combination thereof). The use of such backing prevents immediate wick through and maintains the hydrogel from penetrating the backing too quickly. In addition, the use of such backing provides a patch with a higher yield improvement and superior holdout properties. The use of such backing also obviates the need for a backing liner or a release liner. In such an embodiment, the adhesive patch can exist as a self wound adhesive patch.

As used herein, "holdout" refers to the physical properties of a backing, relating to the ability of a specific class of gels or ointments to penetrate, cross-link, wet, and/or cure within the matrix of the backing. A specific class of gels or ointments may or may not be able to penetrate a given backing. Upon penetration of a gel or ointment into a backing, the gel or ointment will cross-link, wet, or cure in the backing. As such, the holdout properties are a degree of the ability of the gel or ointment to affect the degree of penetration, cross-linking, wetting, and/or curing within the matrix of the backing. Those backings with superior holdout properties will typically prevent, decrease, or lessen the likelihood of the ointment or gel from wetting the backing; will typically increase the likelihood of the ointment or gel to cross-link within the matrix of the backing; will typically increase the likelihood of the ointment or gel to cure within the matrix of the backing; and/or will typically prevent, decrease, or increase the likelihood of the ointment or gel to partially penetrate the matrix of the backing.

It has surprisingly been discovered that the use of a treated backing, such as a fluorocarbon treated non-woven backing, typically increases the yield of an adhesive patch. The use of a backing material that has been treated with a sizing agent allows for the effective control of the rate of penetration, such that the gel or ointment has solidified after it has begun to penetrate the backing, but before it has passed completely through the backing. In addition, the use of a backing material that has been treated with a sizing agent allows for the effective control of the depth to which the ointment or gel will easily penetrate before solidifying. It has surprisingly been discovered that increasing the control of the rate at which the ointment or gel penetrates the backing typically improves the overall yield of the production process by reducing the amount of material which must be discarded because the back side of the backing has become too tacky for either processing or for consumer acceptance.

Referring to FIGS. 1–11, an adhesive patch 1 of the present invention is provided. The adhesive patch 1 includes a therapeutic formulation 5 located on at least a portion of the front side 3 of the backing 2, in at least a portion of the front side 3 of the backing 2, or on and in at least a portion of the front side 3 of the backing 2. Preferably, the therapeutic formulation 5 is partially embedded in at least a portion of the front side 3 of the backing 2. The backing 2 is defined by a front side 3 (the side exposed to the skin during use) and a back side 4 (the side exposed to the environment during use). The backing 2 should be nonirritating to human skin. The backing 2 is a self-supporting sheet of water insoluble, polymeric or natural material that provides strength and integrity for the therapeutic formulation 5. The adhesive patch 1 can be vapor permeable. The backing 2 can also be porous, since porosity provides openings for receiving the therapeutic formulation 5 and it helps to assure that the adhesive skin patch 1 is vapor permeable. Specifically, the backing 2 can retain the therapeutic formulation 5 while allowing moisture from the skin to pass. The backing 2 can have any suitable thickness, provided the suitable thickness allows for a flexible, bendable, pliable, vapor permeable, and/or a stretchable sheet of water insoluble porous material. Specifically, the thickness of the backing 2 can be about 0.001 mm to about 5.0 mm, about 0.001 mm to about 3.0 mm, or about 0.025 mm to about 1.25 mm.

At least a portion of the backing 2 is treated with a hydrophobic sizing agent 8 such that the portion of the backing 2 that is treated with the hydrophobic sizing agent 8 has a surface energy of about 20 dynes/cm$^2$ to about 65 dynes/cm$^2$. Specifically, the portion of the backing 2 that is treated with the hydrophobic sizing agent 8 has a surface energy of about 27 dynes/cm$^2$ to about 56 dynes/cm$^2$. The hydrophobic sizing agent 8 lowers the surface energy of the portion of the backing 2 that is treated with the hydrophobic sizing agent 8. Any suitable hydrophobic sizing agent 8 can be employed, provided the portion of the backing 2 that is treated with the hydrophobic sizing agent 8 has a surface energy of about 20 dynes/cm$^2$ to about 65 dynes/cm2. Suitable hydrophobic sizing agents 8 include, e.g., fluorocarbon solutions, silicone-containing compounds, and combinations thereof. Specifically, the backing 2 can be a non-woven backing 2 that is treated with a fluorocarbon. For example, the fluorocarbon treated backing 2 can be, e.g., VILMED™ M1585 W/HY, VILMED™ M1585H/HY VILMED™ M1586 W/HY, VILMED™ M1586 H/HY, VILMED™ M1570, VILMED™ M1573 F, VILMED™ M1573 FH, VILMED™ M1577 F, VILMED™ M1578 F, or VILMED™ M1578 FH; which are all commercially available from Freudenberg Faservliesstoffe KG (Weinham, Germany). Alternatively, the silicone treated backing 2 can be a non-woven backing 2 that is coated with one or more silicone-containing compounds, e.g., a polydimethyl siloxane, a dialkylsiloxane, a dimethylsiloxo vinyl alkene, a dialkylsiloxo vinyl alkenes, a dimethylsiloxo acrylate, a dialkylsiloxo acrylate, a vinyl terminated polydimethylsiloxane, and a vinyl terminated polydialkylsiloxane.

At least a portion of the backing 2 is treated with the sizing agent 8. The portion of the backing 2 that is treated with the sizing agent 8 is that portion of the backing 2 that can typically include the therapeutic formulation 5. The entire surface of the front side 3 of the backing 2 can be treated with the sizing agent 8 or a portion of the surface of the front side 3 of the backing 2 can be treated with the sizing agent 8. Preferably, the entire surface of the front side 3 of the backing 2 can be treated with the sizing agent 8. In addition to the surface of the front side 3 of the backing 2 being treated with the sizing agent 8, the sizing agent 8 can penetrate at least a portion of the underlying surface (e.g., one-tenth to about nine-tenths the thickness, or about one-fourth to about nine-tenths the thickness) of the backing 2. Specifically, the sizing agent 8 can penetrate the entire underlying surface of the backing 2.

The backing 2 can be manufactured from any suitable material, provided the suitable material can form a flexible, bendable, pliable, and/or stretchable backing 2. The backing 2 includes a flexible porous sheet of water insoluble material that provides support for the adhesive skin patch 1. The backing 2 can include water insoluble polymeric fibers, a porous film, or any other kind of matrix with spaces within the matrix. A specific backing 2 is a lightweight, porous, pliable strip composed of a nonwoven fabric of polymeric or natural fibers such as polyester, cotton or cellulose fibers bonded together with a sizing resin. The backing 2 can be woven or nonwoven. Preferably, the backing 2 includes nonwoven fabric. Specifically, the backing 2 can include polyester, polyurethane, polyolefin, polyamide fibers, natural fibers, cotton fibers, polycellulose fibers, or any mixture thereof. Additional stable, water insoluble flexible sheet materials and methods for manufacturing the suitable backings 2 are disclosed, e.g., in U.S. Pat. No. 4,675,009; U.S. Pat. No. 5,536,263; U.S. Pat. No. 4,696,854; U.S. Pat. No. 5,741,510, and references cited therein, and are suitable as backings 2 according to the present invention. The infusion of the therapeutic formulation 5 into the backing 2 can be accomplished with the use of a continuous process mixer, as disclosed, e.g., in U.S. Pat. No. 5,536,263, and references cited therein; or as discussed herein.

Suitable fluorocarbon treated backings 2 include, e.g., VILMED™ M1585 W/HY, VILMED™ M1585H/HY, VILMED™ M1586 W/HY, VILMED™ M1586 H/HYY, VILMED™ M1570, VILMED™ M1573 F, VILMED™ M1573 FH, VILMED™ M1577 F, VILMED™ M1578 F, and VILMED™ M1578 FH; which are all commercially available from Freudenberg Faservliesstoffe KG (Weinharn, Germany).

Alternatively, the backing 2 can be a non-woven backing 2 that is treated by coating: the front side 3 of the backing 2, the back side 4 of the backing 2, or both the front side 3 and back side 4 of the backing 2; with a silicone-containing compound. Suitable silicone-containing compounds include, e.g., polydimethyl siloxanes, dialkylsiloxanes, dimethylsiloxo vinyl alkenes, dialkylsiloxo vinyl alkenes, dimethylsiloxo acrylates, dialkylsiloxo acrylates, vinyl terminated polydimethylsiloxane, and vinyl terminated polydialkylsiloxane. The exemplary silicone-containing compounds are commercially available from, e.g., Goldschmidt Chemical Corp. (Essen, Germany); GE Silicones (Waterford, N.Y.); Wacker Silicone Corp. (Adrian, Mich.); and Dow Corning Corp. (Midland, Mich.).

The backing 2 can be manufactured from a suitable non-woven fabric that is commercially available from, e.g., Freudenberg Faservliesstoffe KG (Weinham, Germany); Sontara Technologies (division of DuPont Corporation) (Old Hickory, Tenn.); Lystil S.A. (Brignoud Cedex, France); Dexter Nonwovens (Windsor Locks, Conn.); and Chicopee (New Brusnwick, N.J.). Other commercial vendors that supply suitable non-woven woven fabrics can be found at the Technical Textile website (http ://www.technical-textiles.net/technical-textiles-index/orgL.htm).

Figure 10:
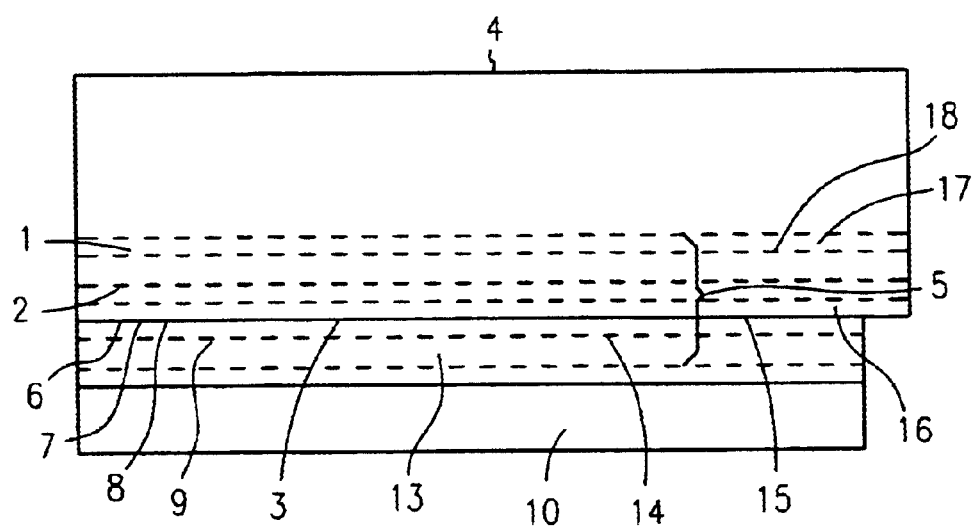
FIG. 10 illustrates an enlarged cross-sectional view of specific patch of the present invention.
Figure 11:
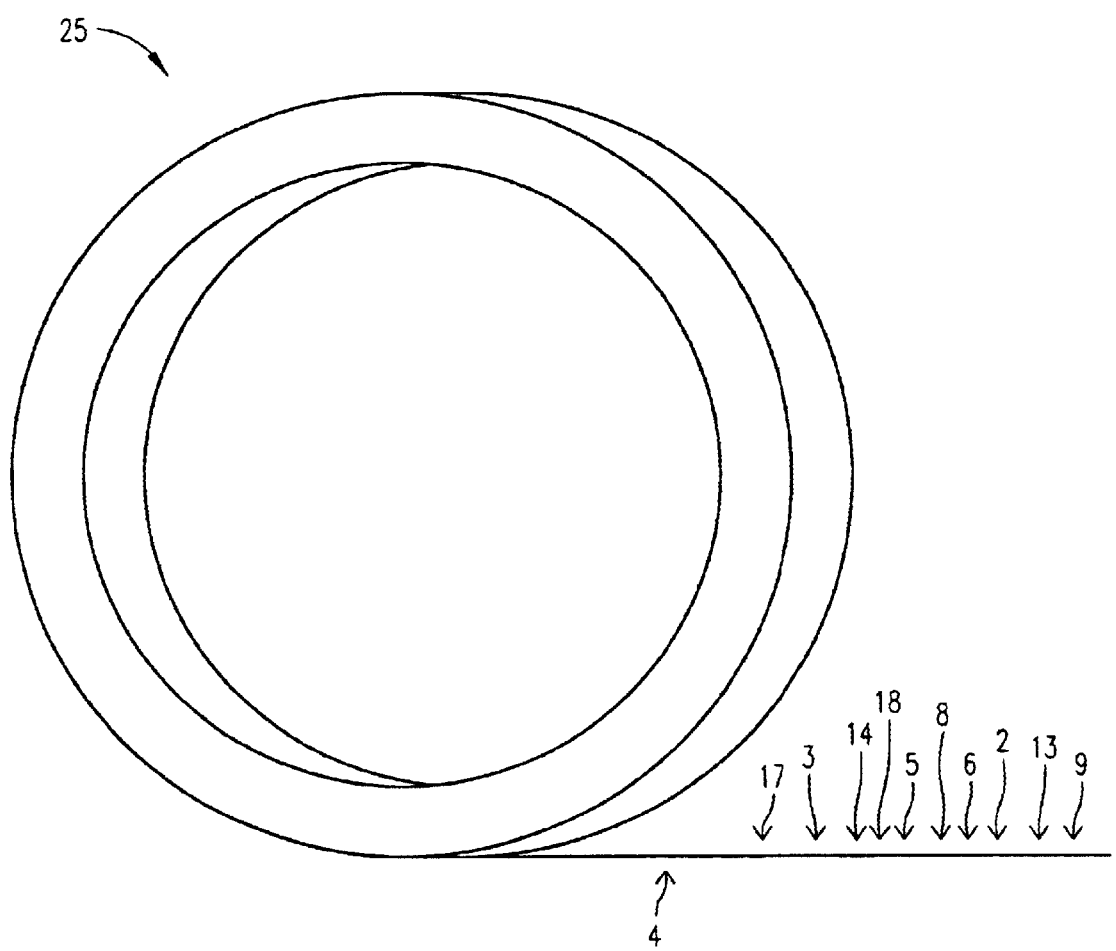
FIG. 11 illustrates a specific adhesive skin patch of the present invention.

As shown in FIGS. 1–6 10, and 11, the backing 2 includes a front side 3 and a back side 4. The adhesive skin patch 1 includes a therapeutic formulation 5 located in at least a portion of the front side 3 of the backing 2, on at least a portion of the front side 3 of the backing 2, or on and in at least a portion of the front side 3 of the backing 2. As such, the therapeutic formulation 5 can be located on the entire surface of the front side 3 of the backing 2 or the therapeutic formulation 5 can be located on a portion of the surface of the front side 3 of the backing 2. Preferably, the therapeutic formulation 5 can be located on the entire surface of the front side 3 of the backing 2. In addition to being located on the surface of the front side 3 of the backing 2, the therapeutic formulation 5 can be located in at least a portion of the underlying surface of the front side 3 of the backing 2 (i.e., the therapeutic formulation 5 can be partially embedded into the backing 2). As shown in FIG. 10, the therapeutic formulation 5 can penetrate a substantial portion of the front side 3 of the backing 2, as disclosed, e.g., in U.S. Pat. No. 5,536,263, and references cited therein. For example, the therapeutic formulation 5 can penetrate about one-tenth to about nine-tenths the thickness of the backing 2, or about one-fourth to about nine-tenths the thickness of the backing 2. As such, the therapeutic formulation 5 can be partially embedded into the backing 2. Preferably, the therapeutic formulation 5 can be located on the entire front side 3 of the backing 2 and partially in the front side 3 of the backing 2 (i.e., the therapeutic formulation 5 is partially embedded into the backing 2). Alternatively, a portion of the front side 3 of the backing 2 can include the therapeutic formulation 5 and other portions of the front side 3 of the backing 2 can include any combination of the pressure sensitive adhesive 14, medicament 15, and solvent 13. For example, a central circular portion of the front side 3 of the backing 2 can include the therapeutic formulation 5 and solvent 13 while the remaining portions of the front side 3 of the backing 2 include only the pressure sensitive adhesive 14. The therapeutic formulation 5, when partially embedded into the front side 3 of the backing 2, imparts strength and structure into the adhesive patch 1. For example, when the therapeutic formulation 5 is partially embedded into the backing 2, the likelihood that the adhesive patch 1 will tear apart when separated from the release liner 10 or when removed from the skin after use, is minimized. When the adhesive skin patch 1 is placed upon the skin of a patient (e.g., human), the therapeutic formulation 5 can be in continuous contact with the skin surface of the patient.

Preferably, the adhesive skin patch 1, upon contact with skin, will allow the skin to breathe. More preferably, the adhesive skin patch 1, upon prolonged contact with skin, will hold in place the therapeutic formulation 5 and will permit the skin to breathe over prolonged periods of time typically experienced with the use of the patch, e.g., up to about 12 hours, up to about 8 hours, or up to about 6 hours.

As shown in FIGS. 3–6 and 10, the adhesive skin patch 1 can be reversibly attached to a release liner 10. The release liner 10 helps to maintain the adhesiveness of the adhesive skin patch 1 prior to use, such as during manufacturing, packaging, shipping, and/or storage. Any suitable release liner 10 can be employed for use in the present invention. Suitable release liners 10 are readily known to those of skill in the art. See, e.g., U.S. Pat. No. 4,675,009; U.S. Pat. No. 5,536,263; U.S. Pat. No. 4,696,854; U.S. Pat. No. 5,741,510, and references cited therein for further descriptions of release liners 10 useful in the present invention. The release liner 10 can include a perforation 12 that allows the tab section 11 of the release liner 10 to be removed (see, FIGS. 3, 5, and 6). Removal of the tab section 11 of the release liner 10 allows the adhesive skin patch 1 to be removed from the release liner 10 with relative ease.

As used herein, a "medicament" is a compound or combination of compounds that effectively prevents and/or treats at least one of psoriasis, dermatitis, and eczema. The medicament 15 can include one or more topical psoriasis drugs, one or more topical dermatitis drugs, one or more topical eczema drugs, or a combination thereof. Any suitable medicament 15 can be employed, provided the medicament 15 effectively treats and/or prevents at least one of psoriasis, dermatitis, and eczema; and the medicament 15 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Suitable medicaments 15 are disclosed, e.g., in *Physician's Desk Reference* (*PDR*), Medical Economics Company (Montvale, N.J.), (53rd Ed.), 1999; *Mayo Medical Center Formulary Unabridged Version*, Mayo Clinic (Rochester, Minn.), January 1998; *Merck Index*, An Encyclopedia of Chemicals, Drugs, and *Biologicals*, (11th Ed.), Merck & Co., Inc. (Rahway, N.J.), 1989; and references cited therein.

The amount of medicament 15 present in the therapeutic formulation 5 will typically depend upon the specific compound or compounds employed as the medicament 15. The medicament 15 can typically be present up to about 99.9 wt. % of the therapeutic formulation 5, up to about 10.0 wt. % of the therapeutic formulation 5, up to 2.0 wt. % of the therapeutic formulation 5, or up to about 1.0 wt. % of the therapeutic formulation 5.

The adhesive skin patch 1 includes a medicament 15 located in at least a portion of the front side 3 of the backing 2, on at least a portion of the front side 3 of the backing 2, or on and in at least a portion of the front side 3 of the backing 2. As such, the medicament 15 can be located on the entire surface of the front side 3 of the backing 2 or the medicament 15 can be located on a portion of the surface of the front side 3 of the backing 2. Preferably, the medicament 15 can be located on the entire surface of the front side 3 of the backing 2. In addition to being located on the surface of the front side 3 of the backing 2, the medicament 15 can be located in at least a portion of the underlying surface of the front side 3 of the backing 2 (i.e., the medicament 15 can be partially embedded into the backing 2). As shown in FIG. 10, the medicament 15 can penetrate a substantial portion of the front side 3 of the backing 2, as disclosed, e.g., in U.S. Pat. No. 5,536,263, and references cited therein. For example, the medicament 15 can penetrate about one-tenth to about nine-tenths the thickness of the backing 2, or about one-fourth to about nine-tenths the thickness of the backing 2. As such, the medicament 15 can be partially embedded into the backing 2. Preferably, the medicament 15 can be located on the entire front side 3 of the backing 2 and partially in the front side 3 of the backing 2 (i.e., the medicament 15 is partially embedded into the backing 2). Alternatively, a portion of the front side 3 of the backing 2 can include the medicament 15 and other portions of the front side 3 of the backing 2 can include any combination of the pressure sensitive adhesive 14 and solvent 13. For example, a central circular portion of the front side 3 of the backing 2 can include the medicament 15 while the remaining portions of the front side 3 of the backing 2 include only the pressure sensitive adhesive 14 and solvent 13. When the adhesive skin patch 1 is placed upon the skin of a patient (e.g., human), the medicament 15 can be in continuous contact with the skin surface of the patient.

As used herein, "psoriasis" refers to an inborn skin disorder typically accompanied by red patches with thick, dry, silvery scales and sometimes swelling of small joints. Psoriasis is caused by the body making too many skin cells. Sores may be anywhere on the body but are more common on the arms, scalp, ears, and the pubic area. *Mosby's Medical Encyclopedia*, The Learning Company, CD-Rom, 1997. It is believed that psoriasis cannot be cured but the conditions associated with psoriasis can be treated.

As used herein, "seborrheic dermatitis" refers to a common, long-term, inflammatory skin disease marked by dry or moist greasy scales and yellowish crusts. Common sites are the scalp, eyelids, face, outer surfaces of the ears, armpits, breasts, groin, and gluteal folds. Kinds of seborrheic dermatitis include cradle cap, dandruff, and seborrheic blepharitis. *Mosby's Medical Encyclopedia*, The Learning Company, CD-Rom, 1997.

As used herein, "eczema" refers to the swelling of the outer skin. The cause of eczema is currently unknown. In the early stage of eczema, the skin may be itchy, red, have small blisters, and be swollen, and weeping. Later it becomes crusted, scaly, and thickened. Eczema is believed not to be a distinct disease. *Mosby's Medical Encyclopedia*, The Learning Company, CD-Rom, 1997.

As used herein, "treat" or "treating" refers to providing relief of one or more of the conditions associated with psoriasis, dermatitis, and/or eczema; or the diminishing or lessening of any one or more of the conditions associated with psoriasis, dermatitis, and/or eczema.

Any suitable topical eczema drug can be employed provided the topical eczema drug effectively treats or prevents eczema. For example, the topical eczema drug can include one or more of camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, and hydrocortisone acetate. See, 21 C.F.R. Ch. 1, Section 348—External Analgesic Drug Products for Over-The-Counter Human Use, Feb. 8, 1983; and 21 C.F.R. Ch. 1, Section 348—External Analgesic Drug Products for Over-The-Counter Human Use, Feb. 27, 1990. In one embodiment, the topical eczema drug can include camphor, menthol or a combination thereof. In another embodiment, the topical eczema drug can include lidocaine, hydrocortisone, or a combination thereof. In yet another embodiment, the topical eczema drug can include lidocaine, hydrocortisone, camphor, menthol, or a combination thereof.

The topical eczema drug can be present in any appropriate and suitable amount. Specifically, the topical eczema drug can be present in about 0.01 wt. % to about 99.9 wt. % of the therapeutic formulation 5. Typically, the amount of topical eczema drug present in the therapeutic formulation 5 will depend upon the specific compound or compounds employed as the topical eczema drug. Preferably, the amount of topical eczema drug will comply with FDA regulations (e.g., 21 C.F.R. Ch. 1, Section 348—External Analgesic Drug Products for Over-The-Counter Human Use, Feb. 8, 1983; and 21 C.F.R. Ch. 1, Section 348—External Analgesic Drug Products for Over-The-Counter Human Use, Feb. 27, 1990; and references cited therein).

For example, as disclosed in Federal Register, Vol. 48, No. 27, § 348, camphor can be present up to about 3.0 wt. % of the therapeutic formulation 5 and menthol can be present up to about 1.0 wt. % of the therapeutic formulation 5. In addition, benzocaine can be present in about 5.0 wt. % to about 20.0 wt. % of the therapeutic formulation 5. Butamben picrate can be present in about 0.5 wt. % to about 1.5 wt. % of the therapeutic formulation 5. Dibucaine can be present in about 0.25 wt. % to about 1.0 wt. % of the therapeutic formulation 5. Dibucaine hydrochloride can be present in about 0.25 wt. % to about 1.0 wt. % of the therapeutic formulation 5. Dimethisoquin hydrochloride can be present in about 0.3 wt. % to about 0.5 wt. % of the therapeutic formulation 5. Dyclonine hydrochloride can be present in about 0.5 wt. % to about 1.0 wt. % of the therapeutic formulation 5. Lidocaine can be present in about 0.5 wt. % to about 4.0 wt. % of the therapeutic formulation 5. Lidocaine hydrochloride can be present in about 0.5 wt. % to about 4.0 wt. % of the therapeutic formulation 5. Pramoxine hydrochloride can be present in about 0.5 wt. % to about 1.0 wt. % of the therapeutic formulation 5. Tetracaine can be present in about 1.0 wt. % to about 2.0 wt. % of the therapeutic formulation 5. Tetracaine hydrochloride can be present in about 1.0 wt. % to about 2.0 wt. % of the therapeutic formulation 5. Benzyl alcohol can be present in about 10.0 wt. % to about 33.0 wt. % of the therapeutic formulation 5. Camphor can be present in about 0.1 wt. % to about 3.0 wt. % of the therapeutic formulation 5. Juniper tar can be present in about 1.0 wt. % to about 5.0 wt. % of the therapeutic formulation 5. Phenolate sodium can be present in about 0.5 wt. % to about 1.5 wt. % of the therapeutic formulation 5. Resorcinol can be present in about 0.5 wt. % to about 3.0 wt. % of the therapeutic formulation 5. Diphenhydramine hydrochloride can be present in about 1.0 wt. % to about 2.0 wt. % of the therapeutic formulation 5. Tripelennamine hydrochloride can be present in about 0.5 wt. % to about 2.0 wt. % of the therapeutic formulation 5. Hydrocortisone can be present in about 0.25 wt. % to about 1.0 wt. % of the therapeutic formulation 5. A corticosteroid can be present in about 0.25 to about 5.0 wt. % of the therapeutic formulation 5. Camphor can be present in about 3 wt. % to about 10.8 wt. % of the therapeutic formulation 5 with phenol in accordance with Federal Register, Vol. 48, No. 27, § 348.20(a)(4). Camphor can be present in about 3 wt. % to about 10.8 wt. % of the therapeutic formulation 5 with metacresol in about 1 wt. % to about 3.6 wt. % of the therapeutic formulation 5, as camphorated metacresol. In addition, hydrocortisone acetate can be present in about 0.25 wt. % to about 1.0 wt. % of the therapeutic formulation 5. See, e.g., 21 C.F.R. Ch. 1, Section 348—External Analgesic Drug Products for Over-The-Counter Human Use, Feb. 8, 1983; and 21 C.F.R. Ch. 1, Section 348—External Analgesic Drug Products for Over-The-Counter Human Use, Feb. 27, 1990.

Any suitable topical psoriasis drug or topical dermatitis drug can be employed provided the topical psoriasis drug or topical dermatitis drug effectively treats or prevents one or more of psoriasis and dermatitis. For example, the topical psoriasis drug or the topical dermatitis drug can include one or more of coal tar, pyrithione zinc, salicylic acid, selenium sulfide, and a pharmaceutically acceptable salt thereof. See, 21 C.F.R. Chapter 1, Section 358, Subpart H—Drug Products for the Control of Dandruff, Seborreic Dermatitis and Psoriasis. Specifically, the topical psoriasis drug or the topical dermatitis drug can include salicylic acid, or a pharmaceutically acceptable salt thereof.

The topical psoriasis drug or the topical dermatitis drug can be present in any suitable amount, provided the amount is effective to treat or prevent psoriasis or dermatitis and the amount remains stable in the therapeutic formulation 5 over a prolonged period of time. Preferably, the stability is over a prolonged period of time, e.g., up to about 3 years, up to about 1 year, or up to about 6 months, typically experienced in the manufacturing, packaging, shipping, and/or storage of the adhesive skin patch 1.

Specifically, the topical psoriasis drug or the topical dermatitis drug can be present in about 0.1 wt. % to about 99.9 wt. % of the therapeutic formulation 5. Typically, the amount of the topical psoriasis drug or the topical dermatitis drug will typically depend upon the specific drug or drugs employed. For example, salicylic acid, or a pharmaceutically acceptable salt thereof, can be present up to about 6.0 wt. % of the therapeutic formulation 5; coal tar can be present up to about 10.0 wt. % of the therapeutic formulation 5; pyrithione zinc can be present up to about 0.5 wt. % of the therapeutic formulation 5; selenium sulfide can be present up to about 2.0 wt. % of the therapeutic formulation 5; and sulfur can be present up to about 10.0 wt. % of the therapeutic formulation 5.

Preferably, the amount of topical psoriasis drug or topical dermatitis drug will comply with FDA regulations. As disclosed in 21 C.F.R. Chapter 1, Section 358, Subpart H—Drug Products for the Control of Dandruff, Seborreic Dermatitis and Psoriasis; salicylic acid, or a pharmaceutically acceptable salt thereof can be present in about 1.8 wt. % to about 3.0 wt. % of the therapeutic formulation 5; coal tar can be present in about 0.5 wt. % to about 5.0 wt. % of the therapeutic formulation 5; pyrithione zinc can be present in about 0.1 wt. % to about 0.25 wt. % of the therapeutic formulation 5; selenium sulfide can be present in about 1.0 wt. %; and sulfur can be present in about 2.0 wt. % to about 5.0 wt. % of the therapeutic formulation 5.

Alternatively, the medicament 15 can include one or more corticosteroids. Any suitable corticosteroid can be employed, provided the corticosteroid effectively treats or prevents one or more of psoriasis, dermatitis, and eczema. Preferably, the suitable corticosteroid is pharmaceutically acceptable for topical use in humans. Suitable corticosteroids are known to those of skill in the art and are disclosed, e.g., in Goodman Gilman, Alfred; Goodman, Louis S.; Gilman, Alfred; *Goodman and Gilman's The Pharmacological Basis of Therapeutics*, Sixth Edition, pp.1482–1486; and Christophers, Enno; Schöpf, Erwin; Kligman, Albert M.; Stoughton, Richard B.; *Topical Corticosteroid Therapy; A Novel Approach to Safer Drugs*, Raven Press, pp. 3–5.

Suitable exemplary corticosteroids include cortisol (hydrocortisone); tetrahydrocortisol; prednisone (cortisone); prednisolone (cortisol); 6α-methylprednisolone; fludrocortisone (9α-fluorocortisol); 11-desoxycortisol; cortisone (11-dehydrocortisol); corticosterone; triamcinolone (9α-fluoro-16α-hydroxyprednisolone); paramethasone (6α-fluoro-16α-methylprednisolone); betamethasone (9α-fluoro-16β-methylprednisolone); dexamethasone (9α-fluoro-16α-methylprednisolone); desoxycorticosterone acetate (doca acetate, percorten acetate); desoxycorticosterone pivalate (percorten pivalate); fludrocortisone acetate (florine acetate); cortisol (hydrocortisone) (cortef, hydrocortone); cortisol acetate (cortef acetate, hydrocortone acetate); cortisol cypionate (cortef); cortisol sodium phosphate (hydrocortone phosphate); cortisol sodium succinate (solucortef); beclopmethasone dipropionate (vanceril); betamethasone (celestone); betamethasone sodium phosphate and acetate (celestone soluspan); betamethasone dipropionate (diprosone); betamethasone valerate (valisone); betamethasone benzoate (benisone, flurodate);

cortisone acetate (cortone acetate); dexamethasone (decadron, gammacorten); dexamethasone sodium phosphate (decadron phosphate, hexadrol phosphate); dexamethasone acetate (decadron-L.A.); fuprednisolone (alphadrol); meprednisone (betapar); methylprednisolone (medrol); methylprednisolone acetate (depo-medrol, medrol acetate); methylprednisolone sodium succinate (solu-medrol); paramethasone acetate (haldrone); prednisolone (delta-cortef); prednisolone acetate (meticortelone acetate); prednisolone sodium phosphate (hydeltrasol); prednisolone sodium succinate (meticortelone soluble); prednisolone tebutate (hydelta-T.B.A.); prednisone (deltasone, paracort); triamcinolone (aristocort, kenacort); triamcinolone acetonide (aristoderm, kenalog); triamcinolone diacetate (aristocort diacetate, kienacort diacetate); triamcinolone hexacotonide (aristospan); desonide (tridesilon); desoximetasone (topicort); flumethasone pivalate (locorten); fluocinolone acetonide (fluonid, synalar); fluocinonide (lidex, topsyn); fluorometholone (oxylone); flurandrenolide (cordran); halcinonide (halog); and medrysone (HMS liquifilm, medrocort). See, e.g., Goodman Gilman, Alfred; Goodman, Louis S.; Gilman, Alfred; *Goodman and Gilman's The Pharmacological Basis of Therapeutics*, Sixth Edition, pp.1482–1486 (Tables 63–3 and 63–4).

Additional suitable exemplary corticosteroids include aclometasone dipropionate (alclovate); betamethasone-17-benzoate (benisone, flurobate); betamethasone dipropionate (diprosone); betamethasone-17-valerate (valisone); clobetasol propionate (temovate); desonide (desowen, tridesilon); dexamethasone (aeroseb-D); desoximetasone (topicort); diflorasone diacetate (florone); flumethasone pivalate (locorten); fluocinolone acetonide (synalar, synalar-HP, neosynalar, fluonid); fluocinolone acetonide acetate (lidex; lidex-E; topsyn); fluorometholone (oxylone); flurandrenolide (cordran); halcinonide (halog); hydrocortisone (cortdome, lubricort); hydrocortisone acetate (cortef, carmol HC, neo-cortef); hydrocortisone-17-valerate (westcort); prednisolone (meti-derm); and triamcinolone acetonide (kenalog, orabase, kenalog-S, mycolog, aristocort, aristocort-A, aristoderm, neo-aristoderm, neo-aristocort). See, e.g., Christophers, Enno; Schöpf, Erwin; Kligman, Albert M.; Stoughton, Richard B.; *Topical Corticosteroid Therapy: A Novel Approach to Safer Drugs*, Raven Press, pp. 3–4 (Table 1).

Additional suitable exemplary corticosteroids include temovate; diprolen; psorcon; temovate; diprolene; cyclocort; diprosone; florone; halog; lidex; maxiflor; topicort; aristocort A; diprosone; florone; maxiflor; valisone; cordran; kenalog; synalar; topicort LP; westcort; cordran; diprosone; kenalog; locold; synalar; valisone; westcort; aclovate; desowen; locorten; synalar; tridesilone; valisone; hydrocortisone; dexamethasone; flumethalone; prednisolone; and methylprednisolone. See, e.g., Christophers, Enno; Schöpf, Erwin; Kligman, Albert M.; Stoughton, Richard B.; *Topical Corticosteroid Therapy: A Novel Approach to Safer Drugs*, Raven Press, p. 5 (Table 2).

Additional suitable exemplary corticosteroids include diprolene and diprosone. See, e.g., Christophers, Enno; Schöpf, Erwin; Kligman, Albert M.; Stoughton, Richard B.; *Topical Corticosteroid Therapy: A Novel Approach to Safer Drugs*, Raven Press, p. 5 (Table 3).

Additional suitable exemplary corticosteroids include augmented betamethasone dipropionate (diprolene); diflorasone diacetate (psorcon); clobetasol propionate (temovate); halobetasol propionate (ultravate); amcinonide (cyclocort); betamethasone dipropionate (diprolene, diprosone); diflorasone diacetate (florone); halcinonide (halog); fluocinonide (lidex); diflorasone diacetate (maxiflor); betamethasone dipropionate (maxivate); diflorasone diacetate (psorcom); desoximetasone (topicort); (aristocort A); amcinonide (cyclocort); betamethasone dipropionate (diprosone); mometasone furoate (elocon); diflorasone diacetate (florone); halcinonide (halog); fluocinonide (lidex-E); diflorasone diacetate (maxiflor); betamethasone dipropionate (maxivate, psorion); betamethasone valerate (valisone); flurandrenolide (cordran); fluticasone propionate (cutivate); mometasone furoate (elocon); triamcinolone acetonide (kenalog); fluocinolone acetonide (synalar); hydrocortisone valerate (westcort); flurandrenolide (cordran); fluticasone propionate (cutivate); betamethasone dipropionate (diprosone); triamcinolone acetonide (kenalog); hydrocortisone butyrate (locoid); fluocinolone acetonide (synalar); betamethasone valerate (valisone); hydrocortisone valerate (westcort); alclometasone dipropionate (aclovate); triamcinolone acetonide (aristocort); desonide (desowen); flumethasone pivalate (locorten); fluocinolone acetonide (synalar); desonide (tridesilon); betamethasone valerate (valisone); hydrocortisone (eldecort, dexamethasone, flumethalone, hydrocortisone, methylprednisolone, or prednisolone); betamethasone; and dexamethasone.

The suitable corticosteroid can be present in any suitable amount, provided the amount of corticosteroid effectively treats or prevents a condition associated with psoriasis, dermatitis, and/or eczema and the amount is stable in the therapeutic formulation 5 over a prolonged period of time typically experienced in the manufacturing, packaging, shipping, and/or the storage of the patch. Preferably, the amount of suitable corticosteroid is pharmaceutically acceptable for topical use in humans. The suitable corticosteroid can be present in about 0.1 wt. % to about 99.9 wt. % of the therapeutic formulation 5. Typically, the amount of corticosteroid present will depend upon the specific corticosteroid or corticosteroids employed in the therapeutic formulation 5. Specifically, the corticosteroid can be up to about 10 wt. %, up to about 5 wt. %, up to about 2 wt. %, up to about 1 wt. %, or up to about 0.1 wt. % of the therapeutic formulation 5. Additionally, the nature and amount of corticosteroid present in the therapeutic formulation 5 should comply with any State and/or Federal guidelines that regulate the use of such compounds (e.g., FDA regulations).

The solvent 13 can act as a carrier for, and preferably can dissolve, the medicament 15 and/or the pressure sensitive adhesive 14. Any suitable solvent 13 can be employed, provided the solvent 13 effectively dissolves the medicament 15 and/or the pressure sensitive adhesive 14 and the solvent 13 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1.

The solvent 13 can include one or more organic compounds, one or more inorganic compounds, or mixtures thereof. Preferably, the solvent 13 will include one or more organic compounds, e.g., esters, terpenes, alcohols, ketones, aldehydes, fatty acids, partially or fully esterified fatty acids, wherein the structures are cyclic, non cylcic (e.g., alkyl), alicyclic (i.e., a bridged ring compound), or aromatic, as well as organic compounds having combinations of these functional groups. Suitable exemplary solvents 13 are disclosed, e.g., in Aldrich Handbook of Fine Chemicals, 2000–2001 (Milwaukee, Wis.).

Preferably, the solvent 13 includes a polyhydric alcohol, water, or a combination thereof. The polyhydric alcohol can be propylene glycol, ethylene glycol, triethylene glycol, or a combination thereof. Additional suitable solvents 13 include, e.g., glycerin; triacetin; 1,3-propane diol; 2-methyl-1,3-propane diol; glycerol ricinoleate; PEG-6 caprylic/capric glycerides; caprylic/capric triglycerides; propyleneglycol dicaprylate/dicaprate; glycerol monostearate; glycerol monocaprylate; glycerol monolaurate; neopentyl alcohol; 1-hexadecanol; hydroxypropyl beta-cyclodextrin; vitamin E; vitamin E acetate; deoxycholic acid; taurodeoxycholic acid; 3-[(3-cholamidopropyl)dimethylammonio]-1-propane-sulfonate; BigCHAP; cholic acid; cholesterol NF; propylene carbonate; lecithin; a pharmaceutically acceptable salt thereof; or a combination thereof.

The solvent 13 can be employed in any suitable amount, provided the amount of solvent 13 is effective to dissolve the medicament 15 and/or the pressure sensitive pressure sensitive adhesive 14 and the effective amount of solvent 13 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Specifically, the solvent 13 can be present in about 1.0 wt % to about 30.0 wt. % or in about 3.0 wt % to about 25.0 wt. % of the therapeutic formulation 5. Typically, the amount of solvent 13 will depend on the compound or compounds employed as the solvent 13. For example, propylene glycol can be present in about 3.0 wt. % to about 11.0 wt. % of the therapeutic formulation 5; water can be present in about 2.0 wt. % to about 20.0 wt. % of the therapeutic formulation 5; and/or triethylene glycol can be present in about 2.0 wt. % to about 20.0 wt. % of the therapeutic formulation 5.

The solvent 13 can be located in at least a portion of the front side 3 of the backing 2, on at least a portion of the front side 3 of the backing 2, or on and in at least a portion of the front side 3 of the backing 2. As such, the solvent 13 can be located on the entire surface of the front side 3 of the backing 2 or the solvent 13 can be located on a portion of the surface of the front side 3 of the backing 2. Preferably, the solvent 13 can be located on the entire surface of the front side 3 of the backing 2. In addition to being located on the surface of the front side 3 of the backing 2, the solvent 13 can be located in at least a portion of the underlying surface of the front side 3 of the backing 2 (i.e., the solvent 13 can be partially embedded into the backing 2). As shown in FIG. 10, the solvent 13 can penetrate a substantial portion of the front side 3 of the backing 2, as disclosed, e.g., in U.S. Pat. No. 5,536,263, and references cited therein. For example, the solvent 13 can penetrate about one-tenth to about nine-tenths the thickness of the backing 2, or about one-fourth to about nine-tenths the thickness of the backing 2. As such, the solvent 13 can be partially embedded into the backing 2. Preferably, the solvent 13 can be located on the entire front side 3 of the backing 2 and partially in the front side 3 of the backing 2 (i.e., the solvent 13 is partially embedded into the backing 2). Alternatively, a portion of the front side 3 of the backing 2 can include the solvent 13 and other portions of the front side 3 of the backing 2 can include any combination of the pressure sensitive adhesive 14 and medicament 15. When the adhesive skin patch 1 is placed upon the skin of a patient (e.g., human), the solvent 13 can be in continuous contact with the skin surface of the patient.

Any suitable pressure sensitive pressure sensitive adhesive 14 can be employed, provided the pressure sensitive pressure sensitive adhesive 14 provides the requisite adhesiveness to the adhesive skin patch 1 and the pressure sensitive adhesive 14 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. It is appreciated that the suitable pressure sensitive adhesives 14 are known to those skilled in the art. Suitable pressure sensitive adhesives 14 are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably the pressure sensitive adhesive 14 is an acrylic ester copolymer.

Any suitable amount of pressure sensitive adhesive 14 can be employed, provided the amount of pressure sensitive adhesive 14 effectively provides the requisite adhesiveness to the adhesive skin patch 1 and the effective amount of the pressure sensitive adhesive 14 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. The therapeutic formulation 5 can include a pressure sensitive adhesive 14 in about 0.1 wt. % to about 50 wt. %, in about 0.5 wt. % to about 10.0 wt. %, or in about 1.0 wt. % to about 15.0 wt. % of the therapeutic formulation 5. Typically, the suitable amount of pressure sensitive adhesive 14 will depend upon the specific pressure sensitive adhesive 14 employed. For example, the pressure sensitive adhesive 14 can include one or more acrylic ester copolymers. Each of the one or more acrylic ester copolymers can be present up to about 20.0 wt. % of the therapeutic formulation 5. Specifically, all of the one or more acrylic ester copolymers, when combined, can be present in about 3.0 wt. % to about 40.0 wt. % of the therapeutic formulation 5, or in about 5.0 wt. % to about 30.0 wt. % of the therapeutic formulation 5. As such, the total amount of acrylic ester copolymers can be about 3.0 wt. % to about 40.0 wt. % of the therapeutic formulation 5, or about 5.0 wt. % to about 30.0 wt. % of the therapeutic formulation 5.

The therapeutic formulation 5 can optionally include one or more humectants 17 to provide a moistening effect to the pressure sensitive adhesive 14. The humectant 17 can optionally hydrate the polymer 9. Any suitable humectant 17 can be employed, provided the humectant 17 effectively provides a moistening effect to the pressure sensitive adhesive 14 and the humectant 17 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. One suitable humectant 17 is glycerin. Other suitable humectants 17 include polyhydric alcohols such as ethylene glycol, propylene glycol, triethylene glycol, tetraethylene glycol, sorbitol, and combinations thereof.

Any suitable amount of humectant 17 can be employed, provided the amount of humectant 17 effectively provides a moistening effect to the pressure sensitive adhesive 14 and the amount of humectant 17 effectively remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Typically, the suitable amount of humectant 17 will depend upon the specific humectant 17 employed and the specific polymer 9 employed. For example, karaya, polyacrylamide, or a combination thereof can be employed as the polymer 9 and glycerin can be employed as the humectant 17, wherein the glycerin is present in about about 25.0 wt. % to about 70.0 wt. % or in about 40.0 wt. % to about 55.0 wt. % of the therapeutic formulation 5.

The therapeutic formulation 5 can optionally include a compound that emulsifies the therapeutic formulation 5. One suitable compound that effectively emulsifies the therapeutic formulation 5 is pectin. The emulsifier (e.g., pectin) can be present in any suitable amount, provided the suitable amount is effective to emulsify the therapeutic formulation 5 and the emulsifier remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Specifically, the emulsifier (e.g., pectin) can be present in about 1.0 wt. % to about 20.0 wt. % of the therapeutic formulation 5, or in about 2.0 wt. % to about 10.0 wt. % of the therapeutic formulation 5.

The pressure sensitive adhesive 14 can optionally include one or more polymers 9. The polymer 9 provides structure and strength to the pressure sensitive adhesive 14 or provides structure and strength to the therapeutic formulation 5. Any suitable polymer 9 can be employed, provided the polymer 9 provides structure and strength to the pressure sensitive adhesive 14 or provides structure and strength to the therapeutic formulation 5, and the polymer 9 remains stable in the therapeutic formulation 5. Preferably, the stability is over a prolonged period of time, e.g., up to about 3 years, up to about 1 year, or up to about 6 months, typically experienced in the manufacturing, packaging, shipping, and/ or storage of the adhesive skin patch 1.

Suitable polymers 9 include natural polymers and synthetic polymers. Specifically, the polymer 9 can include, e.g., karaya, a polyacrylamide, xanthum gum, guar gum, a hydrophilic polymer, a hydrocolloidal polymer, starch, a starch derivative, vinyl acetate copolymer, polyvinyl pyrrolidone, polyethylene oxide, algin, a derivative of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS, or a combination thereof. Other suitable polymers 9 are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably, the polymer 9 can include polyacrylamide, karaya, or a combination thereof.

Any suitable amount of polymer 9 can be employed, provided the amount of polymer 9 effectively provides structure and strength to the pressure sensitive adhesive 14 or to the therapeutic formulation 5, and the effective amount of polymer 9 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Typically, the suitable amount of polymer 9 will depend upon the specific polymer 9 employed. Specifically, karaya can be employed as the polymer 9 in about 5.0 wt. % to about 45 wt. % of the therapeutic formulation 5, or in about 8.0 wt. % to about 40 wt. % of the therapeutic formulation 5; polyacrylamide can be employed as the polymer 9 in about 5.0 wt. % to about 35 wt. % of the therapeutic formulation 5, or in about 8.0 wt. % to about 30 wt. % of the therapeutic formulation 5; or both karaya and polyacrylamide can be employed as the polymer 9, wherein karaya is present in about 5.0 wt. % to about 35 wt. % of the therapeutic formulation 5 and polyacrylamide is present in about 5.0 wt. % to about 30 wt. % of the therapeutic formulation 5.

Alternatively, the pressure sensitive adhesive 14 can include a hot melt pressure sensitive adhesive 14 or solvent based pressure sensitive adhesive 14 (e.g., polyacrylate, polyisobutylene, and polybutene), rubber, silicone based pressure sensitive adhesives 14 (e.g., polydimethylsiloxane and resin mixtures), polystyrene-polybutadiene-polystyrene, polystyrene-polyisoprene-polystyrene, polystyrene-poly (ethylene-butylene)-polystyrene block polymers, or any combination thereof. In addition, the adhesive 14 can include a resin emulsion adhesive, wherein the resin emulsion adhesive can include vinyl acetate resin, acrylic ester copolymer, vinyl actetate/diocyl maleate copolymer, acrylic copolymer, or any combination thereof.

Other suitable pressure sensitive adhesives 14 are disclosed, e.g., in U.S. Pat. No. 4,675,009; U.S. Pat. No. 5,536,263; U.S. Pat. No. 4,696,854; U.S. Pat. No. 5,741,510, and references cited therein.

The pressure sensitive adhesive 14 can be located in at least a portion of the front side 3 of the backing 2, on at least a portion of the front side 3 of the backing 2, or on and in at least a portion of the front side 3 of the backing 2. As such, the pressure sensitive adhesive 14 can be located on the entire surface of the front side 3 of the backing 2 or the pressure sensitive adhesive 14 can be located on a portion of the surface of the front side 3 of the backing 2. Preferably, the pressure sensitive adhesive 14 can be located on the entire surface of the front side 3 of the backing 2. In addition to being located on the surface of the front side 3 of the backing 2, the pressure sensitive adhesive 14 can be located in at least a portion of the underlying surface of the front side 3 of the backing 2 (i.e., the pressure sensitive adhesive 14 can be partially embedded into the backing 2). As shown in FIG. 10, the pressure sensitive adhesive 14 can penetrate a substantial portion of the front side 3 of the backing 2, as disclosed, e.g., in U.S. Pat. No. 5,536,263, and references cited therein. For example, the pressure sensitive adhesive 14 can penetrate about one-tenth to about nine-tenths the thickness of the backing 2, or about one-fourth to about nine-tenths the thickness of the backing 2. As such, the pressure sensitive adhesive 14 can be partially embedded into the backing 2. Preferably, the pressure sensitive adhesive 14 can be located on the entire front side 3 of the backing 2 and partially in the front side 3 of the backing 2 (i.e., the pressure sensitive adhesive 14 is partially embedded into the backing 2). Alternatively, a portion of the front side 3 of the backing 2 can include the pressure sensitive adhesive 14 and other portions of the front side 3 of the backing 2 can include any combination of the solvent 13 and medicament 15. The pressure sensitive adhesive 14, being partially embedded into the front side 3 of the backing 2, imparts strength and structure into the adhesive patch 1. For example, when the pressure sensitive adhesive 14 is partially embedded into the backing 2, the likelihood that the adhesive patch 1 will tear apart when separated from the release liner 10 or when removed from the skin after use, is minimized. When the adhesive skin patch 1 is placed upon the skin of a patient (e.g., human), the pressure sensitive adhesives 14 can be in continuous contact with the skin surface of the patient.

The therapeutic formulation 5 can optionally include one or more fillers 6. Any suitable filler 6 can be employed. Suitable fillers 6 include malto dextrin, dextrin, 70% sorbitol water, modified starches, depolymerized starches, and methylcellulose. As used herein, "malto dextrin" is a dextrose equivalent, wherein dextrose is D-glucose. Malto dextrin is commercially available as Amaizo Lodex 5 from American Maize-Products (Hammond, Ind.). Any suitable amount of filler can be employed in the therapeutic formulation 5. The suitable amount of filler can depend in part upon the specific filler present in the therapeutic formulation 5. For example, malto dextrin can be present up to about 20.0 wt. % of the therapeutic formulation 5, or in about 1.0 wt. % to about 10.0 wt. % of the therapeutic formulation 5.

The therapeutic formulation 5 can optionally include a skin protectant 18 (i.e., topical moisturizer or skin conditioner). Any suitable skin protectant 18 can be employed, provided the skin is effectively protected or moisturized and the skin protectant remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Suitable topical moisturizers 18 include, e.g. calamine, aloe, lanolin, glycerin, Vitamin E, Vitamin E acetate, farnesol, glycyrrhetinic acid, or any combination thereof. Specifically, the suitable skin protectant 18 can include, e.g., calamine, aloe, lanolin, glycerin, Vitamin E, Vitamin E acetate, farnesol, glycyrrhetinic acid, or any combination thereof. Additional suitable topical moisturizers 18 are disclosed, e.g., in U.S. Pat. Nos. 6,096,334; 6,096,033; 5,741,510; 5,536,263; 4,675,009; 4,307,717; 4,274,420; 5,976,565; 5,536,263; and references cited therein.

As used herein, "calamine" is a pink powder of zinc oxide and a skin protectant containing about 98% zinc oxide and about 0.5% ferric oxide; "aloe" is the dried latex of leaves of Curaco Aloe (*Aloe barbadenis* Miller, *Aloe vera* Linne) or Cape Aloe (*Aloe ferox* Miller and hybrids), of the family Liliacaea. Aloe is commercially available as Aloe Vera Gel from Terry Laboratories (Melbourne, Fla.). Aloe Vera Gel is commercially available as Aloe Vera Gel 40× (20.0 wt. % solution in water), Aloe Vera Gel 1× (0.5 wt. % solution in water), Aloe Vera Gel 10× (5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

As used herein, "Vitamin E" is 3,4-dihydro-2,5,7,8-tetramethyl-2-(4,8,12-trimethyltridecyl)-2H-1-benzopyran-6-ol; "Vitamin E acetate" is 3,4-dihydro-2,5,7,8-tetramethyl-2-(4,8,12-trimethyltridecyl)-2H-1-benzopyran-6-ol acetate; "lanolin" is the fat-like secretion of the sebaceous glands of sheep (i.e., complex mixture of esters and polyesters of 33 high molecular weight alcohols and 36 fatty acids) which is deposited onto the wool fibers; "farnesol" is 3,7,11-trimethyl-2,6,10-dodecatrien-1-ol. Farnesol is commercially available from American Radiolabeled Chemicals (ARC) (St. Louis, Mo.), and "glycyrrhetinic acid" is a pentacyclic triterpenoid derivative of the beta-amyrin type and is shown below:

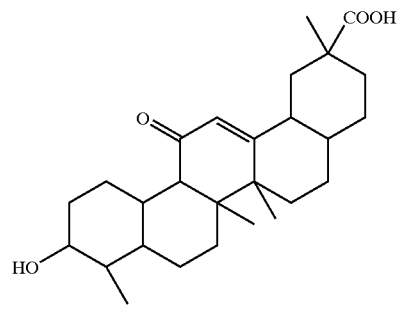

Any suitable amount of skin protectant 18 can be employed, provided the suitable amount of skin protectant 18 effectively protects or moisturizes the skin and the effective amount of skin protectant 18 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Specifically, the skin protectant 18 can be present up to about 20.0 wt. %, up to 10.0 wt. %, up to 5.0 wt. %, or up to 2.0 wt. % of the therapeutic formulation 5. The suitable and effective amount of skin protectant 18 will depend in part upon the specific skin protectant 18 present in the therapeutic formulation 5. For example, Aloe Vera Gel, 10× can be present up to about 20.0 wt. % of the therapeutic formulation 5, up to about 10.0 wt. % of the therapeutic formulation 5, up to about 5.0 wt. % of the therapeutic formulation 5, or up to about 1.0 wt. % of the therapeutic formulation 5. In addition, Vitamin E acetate can be present up to about 10.0 wt. % of the therapeutic formulation 5, up to about 5.0 wt. % of the therapeutic formulation 5, up to about 3.0 wt. % of the therapeutic formulation 5, up to about 2.0 wt. % of the therapeutic formulation 5, or up to about 1.0 wt. % of the therapeutic formulation 5.

The skin protectant 18 can be located in at least a portion of the front side 3 of the backing 2, on at least a portion of the front side 3 of the backing 2, or on and in at least a portion of the front side 3 of the backing 2. As such, the skin protectant 18 can be located on the entire surface of the front side 3 of the backing 2 or the skin protectant 18 can be located on a portion of the surface of the front side 3 of the backing 2. Preferably, the skin protectant 18 can be located on the entire surface of the front side 3 of the backing 2. In addition to being located on the surface of the front side 3 of the backing 2, the skin protectant 18 can be located in at least a portion of the underlying surface of the front side 3 of the backing 2 (i.e., the skin protectant 18 can be partially embedded into the backing 2). As shown in FIG. 10, the skin protectant 18 can penetrate a substantial portion of the front side 3 of the backing 2, as disclosed, e.g., in U.S. Pat. No. 5,536,263, and references cited therein. For example, the skin protectant 18 can penetrate about one-tenth to about nine-tenths the thickness of the backing 2, or about one-fourth to about nine-tenths the thickness of the backing 2. As such, the skin protectant 18 can be partially embedded into the backing 2. Preferably, the skin protectant 18 can be located on the entire front side 3 of the backing 2 and partially in the front side 3 of the backing 2 (i.e., the skin protectant 18 is partially embedded into the backing 2). Alternatively, a portion of the front side 3 of the backing 2 can include the skin protectant 18 and other portions of the front side 3 of the backing 2 can include any combination of the solvent 13, pressure sensitive adhesive 14, and medicament 15. When the adhesive skin patch 1 is placed upon the skin of a patient (e.g., human), the skin protectant 18 can be in continuous contact with the skin surface of the patient.

The therapeutic formulation 5 can optionally include one or more suitable antibiotic agents 16 (i.e., antimicrobial agent). As used herein, an "antibiotic agent" or "antimicrobial agent" is any compound having activity against either Gram-positive or Gram-negative organisms (i.e., inhibits the growth or destroys the development of either Gram-positive or Gram-negative organisms). *Stedman's Medical Dictionary Illustrated*, (25th Ed.), Williams & Wilkins: Baltimore (1990) and *Mosby's Medical, Nursing, & Allied Health Dictionary*, (5th Ed.), Mosby: St. Louis (1998).

Any suitable antibiotic agent 16 can be employed, provided the antibiotic agent 16 effectively inhibits the growth or destroys the development of either Gram-positive or Gram-negative organisms and the antibiotic agent 16 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. Suitable antibiotic agents 16 are disclosed, e.g., in *Physician's Desk Reference* (*PDR*), Medical Economics Company (Montvale, N.J.), (53rd Ed.), 1999; *Mayo Medical Center Forniularv. Unabridged Version*, Mayo Clinic (Rochester, Minn.), Jan. 1998; *Merck Index*, An Encyclopedia of Chemicals, Drugs, and *BioloRicals*, (11th Ed.), Merck & Co., Inc. (Rahway, N.J.), 1989; and references cited therein.

Suitable classes of antibiotic agents 16 include, e.g., β-lactams, aminoglycosides, antifungal agents, and combinations thereof. Suitable antibiotic agents 16 include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenam, meropenem, cilistatin, cefadroxil, cefazolin, cephalexin, cephalothin, cefaclor, cefamandole, cefonicid, cefoxitin, cefuroxine, cefoperazone, cefotaxime, ceftazidime, ceftazidime, ceftizoxime, ceftriaxone, moxalactam, cefepine, bacitracin, vancomycin, aztreonam, amoxicillin, clavulanic acid, benzathine, penicillin g, penicillin v, ampicillin, carbenicillin indamyl, carbenicillin, mezlocillin, piperacillin, ticarcillin, cloxacillin, dicloxacillin, floxacillin, methicillin, nafcillin, oxacillin, colistmethate, polymixin b, trimethoprim, co-trimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythrmoycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, ascariasis, pinworm, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, pharmaceutically acceptable salts thereof, and combinations thereof. Specifically, the antibiotic agent can be erythromycin, tetracycline, clindamycin, cephalosporin, pharmaceutically acceptable salts thereof, or a combination thereof.

Any suitable amount of antibiotic agent 16 can be employed, provided the amount of antibiotic agent 16 employed effectively inhibits the growth or destroys the development of either Gram-positive or Gram-negative organisms and the effective amount of the antibiotic agent 16 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. The antibiotic agent 16 can be present up to about 99.9 wt. % of the therapeutic formulation 5, up to about 50 wt. % of the therapeutic formulation 5, up to about 25 wt. % of the therapeutic formulation 5, or up to about 10 wt. % of the therapeutic formulation 5. Typically, the amount of antibiotic agent 16 will depend upon the specific antibiotic agent 16 employed. Preferably, the antibiotic agent 16 can be present up to about 5.0 wt. % of the therapeutic formulation 5, up to about 1.0 wt. % of the therapeutic formulation 5, or up to about 0.5 wt. % of the therapeutic formulation 5.

The antibiotic agent 16 can be located in at least a portion of the front side 3 of the backing 2, on at least a portion of the front side 3 of the backing 2, or on and in at least a portion of the front side 3 of the backing 2. As such, the antibiotic agent 16 can be located on the entire surface of the front side 3 of the backing 2 or the antibiotic agent 16 can be located on a portion of the surface of the front side 3 of the backing 2. Preferably, the antibiotic agent 16 can be located on the entire surface of the front side 3 of the backing 2. In addition to being located on the surface of the front side 3 of the backing 2, the antibiotic agent 16 can be located in at least a portion of the underlying surface of the front side 3 of the backing 2 (i.e., the antibiotic agent 16 can be partially embedded into the backing 2). As shown in FIG. 10, the antibiotic agent 16 can penetrate a substantial portion of the front side 3 of the backing 2, as disclosed, e.g., in U.S. Pat. No. 5,536,263, and references cited therein. For example, the antibiotic agent 16 can penetrate about one-tenth to about nine-tenths the thickness of the backing 2, or about one-fourth to about nine-tenths the thickness of the backing 2. As such, the antibiotic agent 16 can be partially embedded into the backing 2. Preferably, the antibiotic agent 16 can be located on the entire front side 3 of the backing 2 and partially in the front side 3 of the backing 2 (i.e., the antibiotic agent 16 is partially embedded into the backing 2). Alternatively, a portion of the front side 3 of the backing 2 can include the antibiotic agent 16 and other portions of the front side 3 of the backing 2 can include any combination of the solvent 13, pressure sensitive adhesive 14, and medicament 15. When the adhesive skin patch 1 is placed upon the skin of a patient (e.g., human), the antibiotic agent 16 can be in continuous contact with the skin surface of the patient.

The therapeutic formulation 5 can optionally include an antiseptic 30. As used herein, an "antiseptic" is an agent or substance capable of effecting antisepsis, i.e., the prevention of infection by inhibiting the growth of infectious agents. *Stedman's Medical Dictionary*, 25th Ed., illustrated, Williams & Wilkins, Baltimore, Md., p. 100 (1990). Any suitable antiseptic 30 can be employed, provided the suitable antiseptic 30 effectively inhibits the growth of infectious agents and the effective antiseptic 30 remains stable in the therapeutic formulation 5. Suitable antiseptics 30 include, e.g., triclosan, phenoxy isopropanol, chlorhexidine gluconate, povidone iodine, and any combination thereof.

The antiseptic 30 can be employed in any suitable amount, provided the suitable amount of antiseptic 30 effectively inhibits the growth of infectious agents and maintains the stability of the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. For example, the antiseptic 30 can be employed up to about 20.0 wt. % of the of the therapeutic formulation 5, up to about 10.0 wt. % of the of the therapeutic formulation 5, up to about 1.0 wt. % of the of the therapeutic formulation 5, or up to about 0.1 wt. % of the of the therapeutic formulation 5.

The antiseptic 30 can be located in at least a portion of the front side 3 of the backing 2, on at least a portion of the front side 3 of the backing 2, or on and in at least a portion of the front side 3 of the backing 2. As such, the antiseptic 30 can be located on the entire surface of the front side 3 of the backing 2 or the antiseptic 30 can be located on a portion of the surface of the front side 3 of the backing 2. Preferably, the antiseptic 30 can be located on the entire surface of the front side 3 of the backing 2. In addition to being located on the surface of the front side 3 of the backing 2, the antiseptic 30 can be located in at least a portion of the underlying surface of the front side 3 of the backing 2 (i.e., the antiseptic 30 can be partially embedded into the backing 2). As shown in FIG. 10, the antiseptic 30 can penetrate a substantial portion of the front side 3 of the backing 2, as disclosed, e.g., in U.S. Pat. No. 5,536,263, and references cited therein. For example, the antiseptic 30 can penetrate about one-tenth to about nine-tenths the thickness of the backing 2, or about one-fourth to about nine-tenths the thickness of the backing 2. As such, the antiseptic 30 can be partially embedded into the backing 2. Preferably, the antiseptic 30 can be located on the entire front side 3 of the backing 2 and partially in the front side 3 of the backing 2 (i.e., the antiseptic 30 is partially embedded into the backing 2). Alternatively, a portion of the front side 3 of the backing 2 can include the antiseptic 30 and other portions of the front side 3 of the backing 2 can include any combination of the solvent 13, pressure sensitive adhesive 14, and medicament 15. When the adhesive skin patch 1 is placed upon the skin of a patient (e.g., human), the antiseptic 30 can be in continuous contact with the skin surface of the patient.

The therapeutic formulation 5 can optionally include a preservative 7 that is useful for preventing bacterial growth, mold growth, fermentation, and/or decomposition. As used herein, "preservative" refers to any substance which prevents bacterial growth, mold growth, fermentation, and/or decomposition. *Concise Chemical and Technical Dictionary*, 4th enlarged edition, Chemical Publishing Co., Inc., NY, N.Y. p. 939 (1986). Any suitable preservative 7 can be employed, provided the preservative 7 effectively prevents bacterial growth, mold growth, fermentation, and/or decomposition; and the preservative 7 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the adhesive skin patch 1.

Suitable preservatives 7 include, e.g., quat-15, parabens, dichlorobenzyl alcohol, ethylene diamine tetreacetic acid, formaldehyde, gum benzoin, imidazolidinyl urea, phenylmercuric acetate, poly aminopropyl biguanide, proply gallate, sorbic acid, cresol, chloroacetamide sodium benzoate, chloromethyl-methylisothiazolinone, chloromethyl-methylisothiazolon, chloromethyl-methylisothiazolinone benzalkonium chloride, an octylisothiazolinone benzimidazol-compound, chloromethyl-methylisothiazolinone octylisothiazolinone, o-phenylphenol benzisothiazolinone, o-phenylphenol benzisothiazolinone, benzisothiazolinone, an aliphatic amine of 2-thiopyridineoxide, benzoic acid, editic acid, phenolic acid, benzyl alcohol, isopropyl alcohol, benzenethonium chloride, bronopol, cetrimide, chlorohexidine, chlorobutanol, chlorocresol, phenol, phenoxyethanol, phenyl ethyl alcohol, phenylmercuric acetate, phenylmercuric borate, phenylmercuric nitrate, potassium sorbate, propylene glycol, sodium benzoate, sodium propionate, thimerosol, and pharmaceutically acceptable salts thereof. Preferably, the preservative is quat-15, which is commercially available from Dow Chemical (Midland Mich.); methyl paraben; ascorbic acid; or a combination thereof.

The preservative 7 can be employed in any suitable amount provided the amount of preservative 7 effectively prevents bacterial growth, mold growth, fermentation, and/or decomposition and the effective amount of preservative 7 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. The preservative 7 can be present up to about 99.9 wt. % of the therapeutic formulation 5, up to about 20.0 wt. % of the therapeutic formulation 5, up to 5.0 wt. % of the therapeutic formulation 5, or up to 1.5 wt. % of the therapeutic formulation 5. The amount of preservative 7 present in the therapeutic formulation 5 will typically depend upon the specific compound or compounds employed as the preservative 7. For example, quat-15 can be employed in about 0.01 wt. % to about 1.5 wt. % of the therapeutic formulation 5, in about 0.05 wt. % to about 0.15 wt. % of the therapeutic formulation 5, or in about 0.08 wt. % to about 0.12 wt. % of the therapeutic formulation 5.

In one embodiment of the present invention, the therapeutic formulation 5 can include a component (e.g., medicament 15) that is not soluble and/or stable in the solvent 13, in the amount employed. The use of a complexing agent can be employed to solubilize and/or stabilize these components in the therapeutic formulation 5. Any suitable complexing agent can be employed, provided the complexing agent effectively solubilizes and/or stabilizes these components and the complexing agent remains stable in the therapeutic formulation 5 over a prolonged period of time. Preferably, the stability is over a prolonged period of time, e.g., up to about 3 years, up to about 1 year, or up to about 6 months, typically experienced in the manufacturing, packaging, shipping, and/or storage of the adhesive skin patch 1. In addition, any suitable amount of complexing agent can be employed, provided the amount of complexing agent effectively solubilizes and/or stabilizes these components and the amount of complexing agent remains stable in the therapeutic formulation 5 over a prolonged period of time.

For example, at standard temperature and pressure, corticosteroids such as hydrocortisone are not typically soluble or stable in aqueous solutions. It has surprisingly been discovered, however, that a suitable complexing agent such as a cyclodextrin can be employed to solubilize and/or stabilize the corticosteroid in the aqueous solution. As used herein, a "cyclodextrin" refers to a non-reducing cyclic oligosacoharide with at least 6 anhydroglucose units linked by alpha 1,4 bonds to form a ring. Cyclodextrins are typically produced by the action of the enzyme cyclodextrin glucosyltransferase [CGT-ase ] on starch. The most common cyclodextrins include alpha, beta, and gamma cyclodextrins, which have six, seven, or eight, respectively, anhydroglucose units in the ring structure. All of the hydroxyl groups in cyclodextrins are oriented to the outside of the ring while the glucosidic oxygen and two rings of the non-exchangeable hydrogen atoms are directed towards the interior of the cavity. This combination gives cyclodextrins a hydrophobic inner cavity and a hydrophilic exterior. See, e.g., ML. Bender and M. Komiyama, *Cyclodextrin Chemistry*, Springer, Berlin, 1978.

Cyclodextrins are enzymatically-modified starches formed by the action of the enzyme cyclodextrin glucosyltransferase on starch. They are doughnut-shaped molecules, which can interact with organic molecules to form complexes. It is also possible for some organic molecules and some inorganic salts to associate with the hydroxyl groups of the cyclodextrin. Three cyclodextrins are typically formed, alpha, beta, and gamma cyclodextrin, which contain six, seven, or eight glucose molecules in the ring, respectively. The electron-dense glycosidic oxygen atoms are oriented inward and line the cavity. The hydroxyl groups are directed toward the outside of the ring. These hydrophilic groups interact with the water to give the cyclodextrins their aqueous solubility properties. The hydrogen and glycosidic oxygen atoms lining the cavity give the cyclodextrin molecule its hydrophobic character and its ability to interact with organic molecules to form complexes. Because of the free rotation of the C-6 carbon, this end of the cyclodextrin cavity is narrower than the end with the C-2 and C-3 hydroxyls.

Derivatives of cyclodextrin can be obtained, e.g., by replacing one or more hydroxyl groups with a suitable radical (i.e., pendant group). Suitable pendant groups include, e.g., sulfinyl; sulfonyl; phosphate; $(C_1-C_{12})$alkyl optionally substituted with one or more (e.g., 1, 2, 3, or 4) hydroxy, carboxy, carbonyl, acyl, oxy, oxo; or a combination thereof. Suitable specific pendant groups include methyl, ethyl, hydroxypropyl, carboxymethyl, sulfate, phosphate, and an acrylate. For example, the specific pendant group can include $(C_1-C_{12})$alkoxy optionally substituted with one or more hydroxy.

Specific suitable derivatives of cyclodextrin include, e.g., alpha-cyclodextrin sulfate, beta-cyclodextrin sulfate, gamma-cyclodextrin sulfate, alpha-hydroxypropyl cyclodextrin, beta-hydroxypropyl cyclodextrin, gamma-hydroxypropyl cyclodextrin, alpha-cyclodextrin phosphate, beta-cyclodextrin phosphate, and gamma-cyclodextrin phosphate.

Cyclodextrins are starches that have been specially modified by the action of an enzyme to make a water-soluble ring-shaped molecule, capable of holding another, oil-like organic substance in its 'cavity'. Because of this unique property, cyclodextrins can be used to carry all kinds of active ingredients (e.g., drugs, fragrances, flavors, and vitamins) in a wide variety of formulations. Increased stability, water solubility, and controlled release are among the many application benefits. Specifically, cyclodextrins have the benefit of encapsulating a substance, thereby providing protection for the substance. This results in increased shelf-life and a reduced loss of degradation or decomposition. Cyclodextrins are themselves soluble in water, and can greatly increase the solubility of highly water insoluble substances. In addition, cyclodextrins can be used to control the release of a substance.

Suitable cyclodextrins include alpha cyclodextrins, beta cyclodextrins, and gamma cyclodextrins. Specifically, the cyclodextrin can be hydroxylpropyl beta cyclodextrin, hydroxylproplyl alpha cyclodextrin, or a combination thereof. In addition, the cyclodextrin can optionally be branched.

Suitable cyclodextrins, and derivatives thereof, can be found, e.g., at U.S. Pat. No. 5,376,641; U.S. Pat. No. 5,229,370; U.S. Pat. No. 4,383,992; the Cerestar website (http://www.cerestar.com); the Betadexcyclodextrin website (http://www.betadexcyclodextrin.com); French et al., *Archives in Biochem. and Biophysics*, Volume III, (1965) 153–150; the carbomer website (http://www.carbomer.com) and references cited therein.

The therapeutic formulation 5 can preferably remain stable over the period of time typically experienced with the manufacturing, packaging, shipping, and/or storage of the adhesive skin patch 1, e.g., up to about a month, up to about a year, up to about two years, or up to about 3 years. The stability of the medicament 15, for example, is due in part to the therapeutic formulation 5 including the medicament 15 in an adhesive formulation. The adhesive formulation is preferably a hydrogel that holds the medicament 15 in an available form while maintaining the necessary stability, pressure sensitive adhesion and effectiveness over a prolonged period of time, e.g., up to about a month, up to about a year, up to about two years, or up to about 3 years.

The adhesive skin patch 1 can have any suitable size and shape. In addition, the adhesive skin patch 1 can be cut, as desired, to provide an adhesive skin patch 1 of a desired size and shape. The adhesive skin patch 1 can be cut with any suitable cutting device such as a scissors, scalpel, or knife.

The adhesive skin patch 1 can have any suitable length. In one embodiment of the present invention, the patch can be a self-wound roll 25 without a release liner 10 mounted on the front side 3 of the backing 2 of the adhesive skin patch 1. See, e.g., FIG. 11. In such an embodiment, the adhesive skin patch 1 can have a length of about 12 inches to about 100 yards, about 10 feet to about 50 yards, or about 20 feet to about 20 yards.

In one embodiment of the present invention, the adhesive skin patch 1 can be rectangualar and can have a release liner 10 mounted on the front side 3 of the backing 2 of the adhesive skin patch 1. In such an embodiment, the adhesive skin patch 1 can typically have a length of about 0.1 inch to about 10 inches, of about 0.20 inch to about 8 inches, or about 0.2 inch to about 5.0 inches. Preferably, the adhesive skin patch 1 can have a release liner 10 mounted on the front side 3 of the backing 2 of the adhesive skin patch 1 and can have a length of about 0.2 inch to about 5.0 inches.

The adhesive skin patch 1 can have any suitable width. Typically, the adhesive skin patch 1 will have a width of about 0.1 inch to about 8 inches, of about 0.20 inch to about 4.0 inches, about 0.20 inch to about 2.0 inches, or about 0.20 inch to about 1.0 inch. Preferably, the adhesive skin patch 1 can have a width of about 0.20 inch to about 4.0 inches.

The adhesive skin patch 1 can have any suitable thickness. Typically, the adhesive skin patch 1 will have a thickness of about 0.10 mm to about 2.0 mm, about 0.15 mm to about 1.0 mm, or about 0.20 mm to about 0.75 mm.

In one specific embodiment of the present invention, the adhesive skin patch 1 can be rectangular and can have a length of about 3 inches and a width of about 2 inches. See, e.g., FIG. 7.

Figure 7:
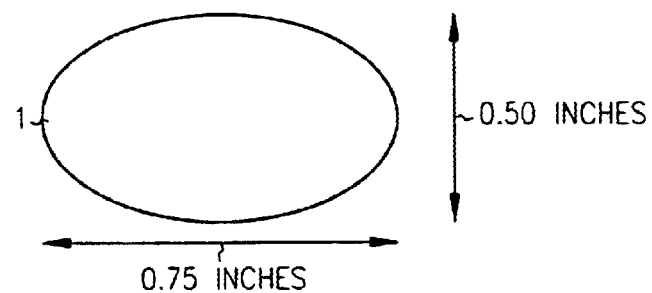
FIG. 7 illustrates a top view of a specific patch of the present invention.
Figure 8:
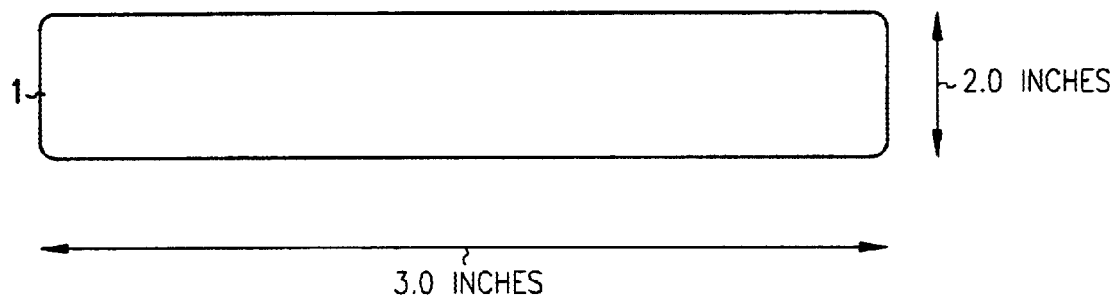
FIG. 8 illustrates a top view of a specific patch of the present invention.

In one specific embodiment of the present invention, the adhesive skin patch 1 can be crescent, oval or circular in shape (see, FIG. 7). The circular adhesive skin patch 1 can have a diameter of about 0.1 inch to about 1.0 inches. Preferably, the circular adhesive skin patch 1 can have a diameter of about 0.25 inch to about 1.0 inch. See, FIG. 7.

In one embodiment of the present invention, the adhesive skin patch 1 can have a release liner 10 mounted on the front side 3 of the backing 2 of the adhesive skin patch 1. In such an embodiment, one or more adhesive skin patches 1 can be mounted on the release liner 10. For example, one adhesive skin patch 1 can have one release liner 10 mounted on the front side 3 of the backing 2 of the adhesive skin patch 1. Alternatively, about 2 to about 100 or about 2 to about 20 adhesive skin patches 1 can be mounted on the release liner 10. The cost of having two or more patches 1 on a single release liner 10 is typically less expensive than skin patches 1 that are separately mounted on a single release liner 10. In addition, some consumers may prefer the ease and comfort of carrying a single patch assembly that includes a single release liner 10 and more than one (e.g., about 2 to about 20, or about 2 to about 10) adhesive patches 1 mounted on the single release liner 10.

Figure 9:
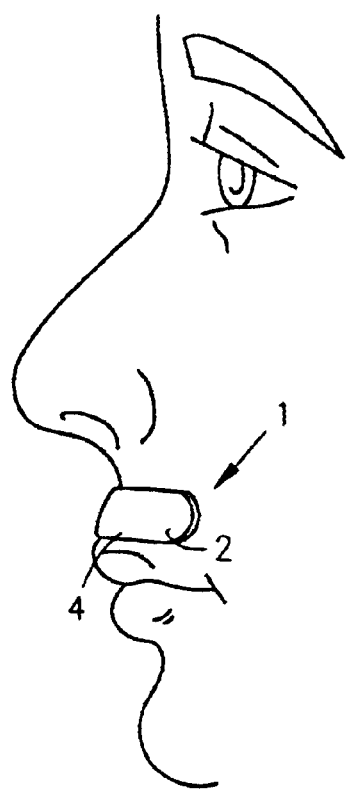
FIG. 9 illustrates a specific patch of the present invention in use.

As shown in FIG. 9, the adhesive skin patch 1 can be applied to the skin surface of a patient. The adhesive skin patch 1 can be applied to any suitable skin surface of the patient. Suitable skin surfaces in which the patch can be applied include, e.g., the head, face, neck, shoulder, chest, back, arm, hand, foot, and leg.

The adhesive patch 1 also serves to effectively exfoliate the skin surface of a mammal (e.g., human). As used herein, "exfoliate" refers to the removal or detachment of superficial cells of an epithelium surface or horny layer (the stratum corneum) of the epidermis. Preferably, the skin cells, upon removal, are dead and are from the outermost one or two layers of the stratum corneum. The therapeutic formulation 5 possesses suitable physical properties (e.g., sufficient adhesiveness) to effectively remove or detach superficial cells of the epithelium surface or stratum corneum of the epidermis. The adhesive skin patch 1 can be applied to the skin surface to be exfoliated for an effective period of time, e.g., from about one second to about twelve hours. After such effective period of time, the adhesive skin patch 1 can be removed from the skin surface. Such exfoliation of the skin is believed to assist in the treatment and/or prevention of psoriasis, dermatitis, and/or eczema. Any suitable skin surface of the mammal can be exfoliated. Suitable skin surfaces of the mammal that can be exfoliated include, e.g., the head, face, neck, shoulder, chest, back, arm, hand, foot, and leg.

The patch serves as a protective covering or barrier. Such protection serves to prevent or diminish the likelihood that foreign objects (e.g., a person's finger, hair, clothing, etc.) will come into contact with the psoriasis, dermatitis, or eczema. This may effectively decrease the likelihood that the skin surface having the psoriasis, dermatitis, and/or eczema will become further irritated or infected.

The patch also serves to aesthetically cover skin blemishes associated with psoriasis, dermatitis, and/or eczema. Since the public perception of psoriasis, dermatitis, and/or eczema is that they are unsightly, many individuals are self conscious and attempt to cover the skin blemishes with products that can further irritate the blemish, thereby worsening the condition. Many of these products do not effectively cover the entire skin blemish for prolonged periods of time (e.g., up to about 8 hours, up to about 6 hours, or up to about 4 hours). The patch allows these individuals to completely cover the skin blemish associated with psoriasis, dermatitis, and/or eczema; thereby concealing the unsightly blemish, while effectively treating the psoriasis, dermatitis, and/or eczema. As such, the patch can serve to aesthetically cover skin blemish such as psoriasis, dermatitis, and/or eczema entirely for prolonged periods of time (e.g., up to about 8 hours, up to about 6 hours, or up to about 4 hours).

The invention will now be illustrated by the following non-limiting Examples.

EXAMPLE #1

| Component | Weight % |
|---|---|
| Karaya | 11.0 |
| Malto Dextrin | 8.0 |
| Pectin | 5.0 |
| Glycerin | 50.0 |
| Propylene Glycol | 6.4 |
| Water | 5.6 |
| Adhesive | 9.5 |
| Salicylic Acid | 2.0 |
| Skin Conditioners | 2.5 |

EXAMPLE #2

| Component | Weight % |
|---|---|
| Polyacrylamide | 16.0 |
| Malto Dextrin | 5.0 |
| Pectin | 4.0 |
| Glycerin | 49.8 |
| Propylene Glycol | 6.6 |
| Water | 6.0 |
| Adhesive | 10.0 |
| Salicylic Acid | 2.0 |
| Skin Conditioners | 0.6 |

EXAMPLE #3

| Component | Weight % |
|---|---|
| Polyacrylamide | 12.0 |
| Malto Dextrin | 7.0 |
| Pectin | 4.0 |
| Glycerin | 47.4 |
| Propylene Glycol | 6.6 |
| Water | 5.6 |
| Adhesive | 13.0 |
| Salicylic Acid | 2.0 |
| Skin Conditioners | 2.4 |

EXAMPLE #4

| Component | Weight % |
|---|---|
| Polyacrylamide | 17.0 |
| Malto Dextrin | 6.0 |
| Pectin | 6.0 |
| Glycerin | 46.6 |
| Propylene Glycol | 9.6 |
| Water | 4.0 |

-continued

| Component | Weight % |
|---|---|
| Adhesive | 2.0 |
| Salicylic Acid | 2.0 |
| Skin Conditioners | 6.8 |

EXAMPLE #5

| Component | Weight % |
|---|---|
| Polyacrylamide | 18.0 |
| Malto Dextrin | 8.0 |
| Pectin | 6.0 |
| Glycerin | 40.0 |
| Propylene Glycol | 5.4 |
| Water | 4.6 |
| Adhesive | 14.0 |
| Salicylic Acid | 2.0 |
| Skin Conditioners | 2.0 |

EXAMPLE #6

| Component | Weight % |
|---|---|
| Polyacrylamide | 4.0 |
| Karaya | 9.0 |
| Malto Dextrin | 7.0 |
| Pectin | 4.0 |
| Glycerin | 49.6 |
| Propylene Glycol | 5.4 |
| Water | 6.2 |
| Adhesive | 10.0 |
| Salicylic Acid | 2.0 |
| Skin Conditioners | 2.8 |

EXAMPLE #7

| Component | Weight % |
|---|---|
| Polyacrylamide | 16.0 |
| Malto Dextrin | 5.2 |
| Pectin | 4.2 |
| Glycerin | 50.0 |
| Propylene Glycol | 6.6 |
| Water | 6.0 |
| Adhesive | 10.0 |
| Salicylic Acid | 2.0 |

EXAMPLE #8

| Component | Weight % |
|---|---|
| Polyacrylamide | 17.0 |
| Malto Dextrin | 6.0 |
| Pectin | 6.0 |
| Glycerin | 46.6 |
| Ethylene Glycol | 9.6 |
| Water | 4.0 |
| Adhesive | 2.0 |
| Salicylic Acid | 2.0 |
| Skin Conditioners | 6.8 |

EXAMPLE #9

| Component | Weight % |
|---|---|
| Polyacrylamide | 16.0 |
| Malto Dextrin | 3.0 |
| Pectin | 2.0 |
| Glycerin | 46.5 |
| Propylene Glycol | 5.6 |
| Water | 8.1 |
| Adhesive | 10.0 |
| Salicylic Acid | 7.0 |
| Skin Conditioners | 1.8 |

EXAMPLE #10

| Component | Weight % |
|---|---|
| Polyacrylamide | 8.0 |
| Malto Dextrin | 5.5 |
| Pectin | 4.0 |
| Glycerin | 49.5 |
| Propylene Glycol | 7.6 |
| Water | 7.0 |
| Adhesive | 15.0 |
| Salicylic Acid | 1.8 |
| Skin Conditioners | 1.6 |

EXAMPLE #11

| Component | Weight % |
|---|---|
| polyacrylamide | 18.0 |
| Malto Dextrin | 8.0 |
| Pectin | 6.0 |
| Glycerin | 40.0 |
| Propylene Glycol | 6.2 |
| Water | 5.6 |
| Adhesive | 14.0 |
| Salicylic Acid | 0.2 |
| Skin Conditioners | 2.0 |

EXAMPLE #12

| Component | Weight % |
|---|---|
| polyacrylamide | 18.0 |
| Malto Dextrin | 7.2 |
| Pectin | 6.0 |
| Glycerin | 40.0 |
| Propylene Glycol | 6.2 |
| Water | 5.6 |
| Adhesive | 14.0 |
| Selenium Sulfide | 1.0 |
| Skin Conditioners | 2.0 |

EXAMPLE #13

| Component | Weight % |
|---|---|
| Polyacrylamide | 10.0 |
| Malto Dextrin | 3.4 |
| Pectin | 2.0 |
| Glycerin | 45.0 |
| Propylene Glycol | 4.6 |
| Water | 18.0 |
| Adhesive | 13.0 |
| Salicylic Acid | 2.0 |
| Skin Conditioners | 2.0 |

EXAMPLE #14

| Component | Weight % |
|---|---|
| Karaya | 18.0 |
| Malto Dextrin | 5.0 |
| Pectin | 3.0 |
| Glycerin | 41.0 |
| Propylene Glycol | 8.4 |
| Water | 7.6 |
| Adhesive | 13.0 |
| Salicylic Acid | 2.0 |
| Skin Conditioners | 2.0 |

EXAMPLE #15

| Component | Weight % |
|---|---|
| Polyacrylamide | 8.0 |
| Malto Dextrin | 7.0 |
| Pectin | 6.0 |
| Glycerin | 48.0 |
| Propylene Glycol | 4.6 |
| Ethylene Glycol | 6.2 |
| Water | 8.0 |
| Adhesive | 6.0 |
| Salicylic Acid | 2.0 |
| Skin Conditioners | 4.2 |

EXAMPLE #16

| Component | Weight % |
|---|---|
| Polyacrylamide | 13.0 |
| Karaya | 6.0 |
| Malto Dextrin | 4.5 |
| Pectin | 2.0 |
| Glycerin | 47.0 |
| Propylene Glycol | 6.6 |
| Water | 7.4 |
| Adhesive | 8.0 |
| Salicylic Acid | 0.5 |
| Skin Conditioners | 5.0 |

EXAMPLE #17

| | |
|---|---|
| Polyacrylamide | 16.0 |
| Malto Dextrin | 6.5 |
| Pectin | 4.0 |
| Glycerin | 49.0 |

-continued

| | |
|---|---|
| Propylene Glycol | 6.6 |
| Water | 5.6 |
| Adhesive | 10.0 |
| Salicylic Acid | 0.5 |
| Skin Conditioners | 1.8 |

EXAMPLE #18

| | |
|---|---|
| Polyacrylamide | 16.0 |
| Malto Dextrin | 5.0 |
| Pectin | 4.0 |
| Glycerin | 50.1 |
| Propylene Glycol | 6.9 |
| Water | 5.5 |
| Adhesive | 10.0 |
| Salicylic Acid | 2.0 |
| Skin Conditioners | 0.4 |

EXAMPLE #19

| Component | Weight % |
|---|---|
| Karaya | 10.0 |
| Malto Dextrin | 8.0 |
| Pectin | 5.0 |
| Glycerin | 42.0 |
| Propylene Glycol | 8.4 |
| Water | 7.6 |
| Adhesive | 9.0 |
| Salicylic Acid | 7.5 |
| Skin Conditioners | 2.5 |

EXAMPLE #20

| Component | Weight % |
|---|---|
| Polyacrylamide | 13.0 |
| Malto Dextrin | 5.0 |
| Pectin | 4.0 |
| Glycerin | 49.6 |
| Propylene Glycol | 9.6 |
| Water | 8.0 |
| Adhesive | 7.0 |
| Salicylic Acid | 2.0 |
| Skin Conditioners | 1.8 |

EXAMPLE #21

| Component | Weight % |
|---|---|
| Polyacrylamide | 8.0 |
| Malto Dextrin | 7.0 |
| Pectin | 6.0 |
| Glycerin | 50.3 |
| Propylene Glycol | 8.6 |
| Water | 6.0 |
| Adhesive | 8.5 |
| Coal Tar | 5.0 |
| Skin Conditioners | 0.6 |

EXAMPLE #22

| Component | Weight % |
|---|---|
| Polyacrylamide | 16.0 |
| Malto Dextrin | 6.5 |
| Pectin | 4.0 |
| Glycerin | 49.8 |
| Propylene Glycol | 6.6 |
| Water | 6.0 |
| Adhesive | 10.0 |
| Salicylic Acid | 0.5 |
| Skin Conditioners | 0.6 |

EXAMPLE #23

| Component | Weight % |
|---|---|
| Polyacrylamide | 9.0 |
| Malto Dextrin | 5.0 |
| Pectin | 4.0 |
| Glycerin | 47.8 |
| Propylene Glycol | 6.6 |
| Water | 12.0 |
| Adhesive | 8.0 |
| Salicylic Acid | 5.0 |
| Skin Conditioners | 2.6 |

EXAMPLE #24

| Component | Weight % |
|---|---|
| Polyacrylamide | 12.0 |
| Malto Dextrin | 7.5 |
| Pectin | 4.0 |
| Glycerin | 48.4 |
| Propylene Glycol | 6.9 |
| Water | 5.6 |
| Adhesive | 13.0 |
| Salicylic Acid | 0.2 |
| Skin Conditioners | 2.4 |

EXAMPLE #25

| Component | Weight % |
|---|---|
| Polyacrylamide | 8.0 |
| Malto Dextrin | 7.0 |
| Pectin | 6.0 |
| Glycerin | 51.8 |
| Propylene Glycol | 8.6 |
| Water | 6.0 |
| Adhesive | 10.0 |
| Salicylic Acid | 2.0 |
| Skin Conditioners | 0.6 |

EXAMPLE #26

| Component | Weight % |
|---|---|
| Polyacrylamide | 16.0 |
| Malto Dextrin | 5.0 |
| Pectin | 4.0 |
| Glycerin | 49.0 |
| Propylene Glycol | 6.6 |
| Water | 5.6 |
| Adhesive | 10.0 |
| Salicylic Acid | 2.0 |
| Skin Conditioners | 1.8 |

EXAMPLE #27

| Component | Weight % |
|---|---|
| Polyacrylamide | 13.0 |
| Karaya | 16.0 |
| Malto Dextrin | 2.0 |
| Pectin | 3.0 |
| Glycerin | 44.6 |
| Propylene Glycol | 5.4 |
| Water | 5.2 |
| Adhesive | 5.0 |
| Salicylic Acid | 2.0 |
| Skin Conditioners | 3.8 |

EXAMPLE #29

| Component | Weight % |
|---|---|
| Polyacrylamide | 25.0 |
| Malto Dextrin | 2.0 |
| Pectin | 2.0 |
| Glycerin | 45.0 |
| Propylene Glycol | 8.4 |
| Water | 4.6 |
| Adhesive | 9.0 |
| Salicylic Acid | 2.0 |
| Skin Conditioners | 2.0 |

EXAMPLE #30

| Component | Weight % |
|---|---|
| Karaya | 24.0 |
| Malto Dextrin | 5.0 |
| Pectin | 3.0 |
| Glycerin | 42.0 |
| Propylene Glycol | 5.4 |
| Water | 5.6 |
| Adhesive | 9.0 |
| Salicylic Acid | 2.0 |
| Skin Conditioners | 4.0 |

EXAMPLE #31

| Component | Weight % |
|---|---|
| Glycerin | 43.5 |
| Q-15 | 0.03 |
| Aloe Vera, 10X | 0.4 |
| Hydrocortisone | 1.0 |
| Lidocaine | 4.0 |
| Methyl Paraben | 0.5 |
| Triethylene Glycol | 7.5 |
| Water | 1.35 |
| Adhesive | 14.72 |
| Karaya | 27.0 |

EXAMPLE #32

| Component | Weight % |
|---|---|
| Adhesive | 10.720% |
| Aloe Vera, 10X | 0.400% |
| Glycerin | 37.610% |
| Hydrocortisone Acetate | 1.116% |
| KARAYA | 27.000% |
| Methyl Paraben | 0.750% |
| Q-15 | 0.030% |
| Triethylene glycol | 5.000% |
| Water | 5.890% |

EXAMPLE #33

| Component | Weight % |
|---|---|
| Adhesive | 10.720% |
| Aloe Vera, 10X | 0.400% |
| Glycerin | 37.610% |
| Hydrocortisone Acetate | 1.116% |
| Methyl Paraben | 0.750% |
| Polyacrlyamide | 27.000% |
| Q-15 | 0.030% |
| Triethylene glycol | 5.000% |
| Water | 5.890% |

EXAMPLE #34

| Component | Weight % |
|---|---|
| Adhesive | 10.500% |
| Aloe Vera, 10X | 30.000% |
| Glycerin | 30.000% |
| Hydrocortisone Acetate | 1.116% |
| Methyl Paraben | 0.384% |
| Polyacrlyamide | 27.000% |
| Q-15 | 0.000% |
| Triethylene glycol | 1.000% |
| Water | 0.000% |

EXAMPLE #35

| Component | Weight % |
|---|---|
| Adhesive | 10.604% |
| Aloe Vera, 10X | 0.500% |
| Glycerin | 30.000% |
| Hydrocortisone Acetate | 1.116% |
| Methyl Paraben | 0.500% |
| Polyacrlyamide | 21.780% |
| Q-15 | 0.500% |
| Triethylene glycol | 5.000% |
| Water | 30.000% |

EXAMPLE #36

| Component | Weight % |
|---|---|
| Adhesive | 50.000% |
| Aloe Vera, 10X | 0.000% |
| Ascorbic Acid | 0.500% |
| Glycerin | 30.000% |
| Hydrocortisone Acetate | 1.116% |
| KARAYA | 17.384% |
| Q-15 | 0.000% |
| Triethylene glycol | 1.000% |
| Water | 0.000% |

EXAMPLE #37

| Component | Weight % |
|---|---|
| Adhesive | 10.000% |
| Aloe Vera, 10X | 1.000% |
| Glycerin | 31.634% |
| Hydrocortisone Acetate | 1.116% |
| KARAYA | 40.000% |
| Methyl Paraben | 0.750% |
| Q-15 | 0.500% |
| Triethylene glycol | 5.000% |
| Water | 10.000% |

EXAMPLE #38

| Component | Weight % |
|---|---|
| Adhesive | 50.000% |
| Aloe Vera, 10X | 0.000% |
| Ascorbic Acid | 0.500% |
| Glycerin | 30.000% |
| Hydrocortisone Acetate | 1.116% |
| Polyacrlyamide | 17.384% |
| Q-15 | 0.000% |
| Triethylene glycol | 1.000% |
| Water | 0.000% |

EXAMPLE #39

| Component | Weight % |
|---|---|
| Adhesive | 10.720% |
| Aloe Vera, 10X | 0.400% |
| Glycerin | 49.210% |
| Hydrocortisone | 1.000% |
| KARAYA | 27.000% |
| Methyl Paraben | 0.750% |
| Q-15 | 0.030% |
| Triethylene glycol | 5.000% |
| Water | 5.890% |

EXAMPLE #40

| Component | Weight % |
|---|---|
| Adhesive | 10.500% |
| Aloe Vera, 10X | 30.000% |
| Glycerin | 30.000% |
| Hydrocortisone | 1.000% |
| KARAYA | 27.000% |
| Methyl Paraben | 0.500% |
| Triethylene glycol | 1.000% |

EXAMPLE #41

| Component | Weight % |
|---|---|
| Adhesive | 10.720% |
| Aloe Vera, 10X | 0.500% |
| Glycerin | 30.000% |
| Hydrocortisone | 1.000% |
| KARAYA | 21.780% |
| Methyl Paraben | 0.500% |
| Q-15 | 0.500% |
| Triethylene glycol | 5.000% |
| Water | 30.000% |

EXAMPLE #42

| Component | Weight % |
|---|---|
| Adhesive | 31.500% |
| Aloe Vera, 10X | 0.500% |
| Glycerin | 30.000% |
| Hydrocortisone | 1.000% |
| KARAYA | 5.000% |
| Methyl Paraben | 0.500% |
| Q-15 | 0.500% |
| Triethylene glycol | 1.000% |
| Water | 30.000% |

EXAMPLE #43

| Component | Weight % |
|---|---|
| Adhesive | 10.720% |
| Aloe Vera, 10X | 0.400% |
| Glycerin | 49.210% |
| Hydrocortisone | 1.000% |
| Methyl Paraben | 0.750% |
| Polyacrlyamide | 27.000% |
| Q-15 | 0.030% |
| Triethylene glycol | 5.000% |
| Water | 5.890% |

EXAMPLE #44

| Component | Weight % |
|---|---|
| Adhesive | 50.000% |
| Ascorbic Acid | 0.500% |
| Glycerin | 30.000% |
| Hydrocortisone | 1.000% |
| Polyacrlyamide | 17.500% |
| Q-15 | 0.000% |
| Triethylene glycol | 1.000% |

EXAMPLE #45

| Component | Weight % |
|---|---|
| Adhesive | 5.000% |
| Aloe Vera, 10X | 0.400% |
| Glycerin | 70.000% |
| Hydrocortisone | 1.000% |
| Polyacrlyamide | 21.570% |
| Q-15 | 0.030% |
| Triethylene glycol | 1.000% |
| Water | 1.000% |

EXAMPLE #46

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |
| Karaya | 24.000% |
| Q-15 | 0.010% |
| Ascorbic acid | 4.000% |
| Water | 21.670% |

EXAMPLE #47

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |
| Karaya | 24.000% |
| Q-15 | 0.010% |
| Ascorbic acid | 4.000% |
| Water | 21.670% |

EXAMPLE #48

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |
| Karaya | 24.000% |
| Propylene Glycol | 5.000% |
| Q-15 | 0.010% |
| Ascorbic acid | 4.000% |
| Water | 16.670% |

EXAMPLE #49

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |

| Component | Weight % |
|---|---|
| Karaya | 24.000% |
| Propylene Glycol | 1.000% |
| Q-15 | 0.010% |
| Ascorbic acid | 4.000% |
| Water | 20.670% |

EXAMPLE #50

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |
| Karaya | 24.000% |
| Propylene Carbonate | 0.200% |
| Propylene Glycol | 0.800% |
| Q-15 | 0.010% |
| Ascorbic acid | 4.000% |
| Water | 20.670% |

EXAMPLE #51

| Component | Weight % |
|---|---|
| Adhesive | 10.720% |
| Aloe Vera, 10X | 0.400% |
| Beta-cyclodextrin | 8.200% |
| Glycerin | 30.000% |
| Hydrocortisone | 1.000% |
| Karaya | 24.000% |
| Propylene Carbonate | 1.000% |
| Propylene Glycol | 4.000% |
| Q-15 | 0.010% |
| Ascorbic acid | 4.000% |
| Water | 16.670% |

EXAMPLE #52

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Karaya | 24.000% |
| Q-15 | 0.010% |
| Ascorbic acid | 4.000% |
| Water | 17.470% |

EXAMPLE #53

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Q-15 | 0.010% |
| Polyacrylamide | 24.000% |
| Ascorbic acid | 4.000% |
| Water | 17.470% |

EXAMPLE #54

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Q-15 | 0.010% |
| Propylene Glycol | 5.000% |
| Polyacrylamide | 24.000% |
| Ascorbic acid | 4.000% |
| Water | 12.470% |

EXAMPLE #55

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Q-15 | 0.010% |
| Propylene Glycol | 1.000% |
| Polyacrylamide | 24.000% |
| Ascorbic acid | 4.000% |
| Water | 16.470% |

EXAMPLE #56

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Q-15 | 0.010% |
| Propylene Carbonate | 0.200% |
| Propylene Glycol | 0.800% |
| Polyacrylamide | 24.000% |
| Ascorbic acid | 4.000% |
| Water | 16.470% |

EXAMPLE #57

| Component | Weight % |
|---|---|
| Adhesive | 10.720% |
| Aloe Vera, 10X | 0.400% |
| Beta-cyclodextrin | 12.400% |
| Glycerin | 30.000% |
| Hydrocortisone | 1.000% |
| Q-15 | 0.010% |
| Propylene Carbonate | 1.000% |
| Propylene Glycol | 4.000% |
| Polyacrylamide | 24.000% |
| Ascorbic acid | 4.000% |
| Water | 12.470% |

The following example can be performed:

EXAMPLE 58

Yield Improvement Data

A. Non-woven Backing Not Treated with a Sizing Agent

The adhesive patch is produced by mixing the ointment or gel of Example 1 in a mixer, then expelling the ointment or gel in a fluid state from the mixer onto the exposed front surface of a N7601 non-woven backing sheet, which is commercially available from Dexter Nonwovens (Windsor Locks, Conn.). The fluid ointment or gel is then spread over the exposed surface of the backing sheet using an appropriate direct coating technique, such as knife-over-roll. A significant amount, if not all of the material that is produced has an unacceptably tacky surface on the back side of the backing. As such, the yield is less than 100% of the theoretical amount of product obtained.

B. Non-woven Backing Treated with a Sizing Agent

The adhesive patch is produced by mixing the ointment or gel of Example 1 in a mixer, then expelling the ointment or gel in a fluid state from the mixer onto the exposed front surface of a VILMED™ M1585 W/HY non-woven backing sheet that is pre-treated with a fluorocarbon. The pre-treated non-woven backing sheet is commercially available from Freudenberg Faservliesstoffe KG (Weinham, Germany). The fluid ointment or gel is then spread over the exposed surface of the backing sheet using an appropriate direct coating technique, such as knife-over-roll. The yield rate is greater than the yield rate above employing the backing that is not treated with a sizing agent.

The adhesive patch 1 of the present invention can be formulated or manufactured employing the above components. The adhesive patch 1 of the present invention can be formulated or manufactured using any suitable technique. Preferably, the adhesive patch 1 can be formulated or manufactured as described herein or as described in U.S. Pat. No. 5,536,263; U.S. Pat. No. 5,741,510; and references cited therein; wherein the oil premix includes the medicament 15, propylene glycol, and solvent 13; the glycerin premix includes glycerin, Vitamin E, and aloe vera gel; and the adhesive premix includes the adhesive, polymer 9, and water; and wherein the backing is treated with a sizing agent 8 prior to the infusion of the therapeutic formulation 5.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An adhesive patch comprising a flexible backing having a front side and a back side and a therapeutic formulation positioned on at least a portion of the front side of the backing, in at least a portion of the front side of the backing, or on and in at least a portion of the front side of the backing; wherein at least a portion of the backing is treated with a sizing agent such that the portion of the backing that is treated with the sizing agent has a surface energy of about 20 dynes/cm$^2$ to about 65 dynes/cm$^2$; wherein the therapeutic formulation comprises:

a medicament selected from one or more topical psoriasis drugs, one or more topical dermatitis drugs, one or more topical eczema drugs, or a combination thereof;

a solvent that dissolves the medicament; and a pressure sensitive adhesive.

2. The adhesive patch of claim 1 wherein the therapeutic formulation is partially embedded in at least a portion of the front side of the backing.

3. The adhesive patch of claim 1 wherein the therapeutic formulation is located on the entire surface of the front side of the backing.

4. The adhesive patch of claim 1 wherein the backing is porous.

5. The adhesive patch of claim 1 wherein the backing is vapor permeable.

6. The adhesive patch of claim 1 wherein the backing comprises water insoluble material.

7. The adhesive patch of claim 1 wherein the backing has a thickness of about 0.025 mm to about 1.25 mm.

8. The adhesive patch of claim 1 wherein the backing comprises a nonwoven fabric.

9. The adhesive patch of claim 1 wherein the sizing agent is a fluorocarbon solution, a silicone-containing compound, or a combination thereof.

10. The adhesive patch of claim 9 wherein the silicone-containing compound is a polydimethyl siloxane, a dialkylsiloxane, a dimethylsiloxo vinyl alkene, a dialkylsiloxo vinyl alkene, a dimethylsiloxo acrylate, a dialkylsiloxo acrylate, a vinyl terminated polydimethylsiloxane, a vinyl terminated polydialkylsiloxane, or a combination thereof.

11. The adhesive patch of claim 1 wherein the entire front side of the backing is treated with the sizing agent.

12. The adhesive patch of claim 1 wherein the sizing agent penetrates at least a portion of the underlying surface of the front side of the backing.

13. The adhesive patch of claim 1 wherein the sizing agent penetrates the entire underlying surface of the front side of the backing.

14. The adhesive patch of claim 1 wherein the entire backing is treated with the sizing agent.

15. The adhesive patch of claim 1 wherein the backing comprises polycellulose fibers, polyester fibers, polyurethane fibers, polyolefin fibers, polyamide fibers, cotton fibers, copolyester fibers, or any mixture thereof.

16. The adhesive patch of claim 1 wherein upon contact with skin, the backing retains the therapeutic formulation and the patch allows moisture from the skin to pass.

17. The adhesive patch of claim 1 wherein the topical psoriasis drug or the topical dermatitis drug is coal tar, pyrithione zinc, salicylic acid, selenium sulfide, a pharmaceutically acceptable salt thereof, or a combination thereof.

18. The adhesive patch of claim 1 wherein the topical psoriasis drug or the topical dermatitis drug is salicylic acid, or a pharmaceutically acceptable salt thereof.

19. The adhesive patch of claim 18 wherein the salicylic acid, or the pharmaceutically acceptable salt thereof is present in about 0.5 wt. % to about 5.0 wt. % of the therapeutic formulation.

20. The adhesive patch of claim 18 wherein the salicylic acid, or the pharmaceutically acceptable salt thereof is present in about 1.8 wt. % to about 3.0 wt. % of the therapeutic formulation.

21. The adhesive patch of claim 1 wherein the topical eczema drug is camphor, menthol, benzocaine, butamben picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, hydrocortisone acetate, or a combination thereof.

22. The adhesive patch of claim 21 wherein the camphor is present up to about 3.0 wt. % of the therapeutic formulation and menthol is present up to about 1.0 wt. % of the therapeutic formulation; benzocaine is present in about 5.0 wt. % to about 20.0 wt. % of the therapeutic formulation; butamben picrate is present in about 0.5 wt.% to about 1.5 wt.% of the therapeutic formulation; dibucaine is present in about 0.25 wt. % to about 1.0 wt. % of the therapeutic formulation; dibucaine hydrochloride is present in about 0.25 wt. % to about 1.0 wt. % of the therapeutic formulation; dimethisoquin hydrochloride is present in about 0.3 wt. % to about 0.5 wt. % of the therapeutic formulation; dyclonine hydrochloride is present in about 0.5 wt. % to about 1.0 wt. % of the therapeutic formulation; lidocaine is present in about 0.5 wt. % to about 4.0 wt. % of the therapeutic formulation; lidocaine hydrochloride is present in about 0.5 wt. % to about 4.0 wt. % of the therapeutic formulation; pramoxine hydrochloride is present in about 0.5 wt. % to about 1.0 wt. % of the therapeutic formulation; tetracaine is present in about 1.0 wt. % to about 2.0 wt. % of the therapeutic formulation; tetracaine hydrochloride is present in about 1.0 wt. % to about 2.0 wt. % of the therapeutic formulation; benzyl alcohol is present in about 10.0 wt. % to about 33.0 wt. % of the therapeutic formulation; camphor is present in about 0.1 wt. % to about 3.0 wt. % of the therapeutic formulation; juniper tar is present in about 1.0 wt. % to about 5.0 wt. % of the therapeutic formulation; phenolate sodium is present in about 0.5 wt. % to about 1.5 wt. % of the therapeutic formulation; resorcinol is present in about 0.5 wt. % to about 3.0 wt. % of the therapeutic formulation; diphenhydramine hydrochloride is present in about 1.0 wt. % to about 2.0 wt. % of the therapeutic formulation; tripelennamine hydrochloride is present in about 0.5 wt. % to about 2.0 wt. % of the therapeutic formulation; hydrocortisone is present in about 0.25 wt. % to about 1.0 wt. % of the therapeutic formulation; corticosteroid is present in about 0.25 to about 5.0 wt. % of the therapeutic formulation; camphor is present in about 3 wt. % to about 10.8 wt. % of the therapeutic formulation with phenol; camphor is present in about 3 wt. % to about 10.8 wt. % of the therapeutic formulation with metacresol in about 1 wt. % to about 3.6 wt. % of the therapeutic formulation, as camphorated metacresol; or hydrocortisone acetate is present in about 0.25 wt. % to about 1.0 wt. % of the therapeutic formulation.

23. The adhesive patch of claim 21 wherein the hydrocortisone, the hydrocortisone acetate, or the combination thereof is present in about 0.25 wt. % to about 1.0 wt. % of the therapeutic formulation.

24. The adhesive patch of claim 21 wherein and the lidocaine, lidocaine hydrochloride, or the combination thereof is present in about 0.5 wt. % to about 4.0 wt. % of the therapeutic formulation.

25. The adhesive patch of claim 1 wherein the medicament is a corticosteroid.

26. The adhesive patch of claim 25 wherein the corticosteroid is at least one of cortisol (hydrocortisone); tetrahydrocortisol; prednisone (cortisone); prednisolone (cortisol); 6α-methylprednisolone; fludrocortisone (9α-fluorocortisol); 11-desoxycortisol; cortisone (11-dehydrocortisol); corticosterone; triamcinolone (9α-fluoro-16α-hydroxyprednisolone); paramethasone (6α-fluoro-16α-methylprednisolone); betamethasone (9α-fluoro-16β-methylprednisolone); dexamethasone (9α-fluoro-16α-methylprednisolone); desoxycorticosterone acetate (doca acetate, percorten acetate); desoxycorticosterone pivalate (percorten pivalate); fludrocortisone acetate (flonne acetate); cortisol (hydrocortisone) (cortef, hydrocortone); cortisol acetate (cortef acetate, hydrocortone acetate); cortisol cypionate (cortef); cortisol sodium phosphate (hydrocortone phosphate); cortisol sodium succinate (solu-cortef); beclopmethasone dipropionate (vanceril); betamethasone (celestone); betamethasone sodium phosphate and acetate (celestone soluspan); betamethasone dipropionate (diprosone); betamethasone valerate (valisone); betamethasone benzoate (benisone, flurodate); cortisone acetate (cortone acetate); dexamethasone (decadron, gammacorten); dexamethasone sodium phosphate (decadron phosphate, hexadrol phosphate); dexamethasone acetate (decadron-L.A.); fuprednisolone (alphadrol); meprednisone (betapar); methylprednisolone (medrol); methylprednisolone acetate (depo-medrol, medrol acetate); methyiprednisolone sodium succinate (solu-medrol); paramethasone acetate (haldrone); prednisolone (delta-cortef); prednisolone acetate (meticortelone acetate); prednisolone sodium phosphate (hydeltrasol); prednisolone sodium succinate (meticortelone soluble); prednisolone tebutate (hydelta-T.B.A.); prednisone (deltasone, paracort); triamcinolone (aristocort, kenacort); triamcinolone acetonide (aristoderm, kenalog); triamcinolone diacetate (aristocort diacetate, kienacort diacetate); triamcinolone hexacotonide (aristospan); desonide (tridesilon); desoximetasone (topicort); flumethasone pivalate (locorten); fluocinolone acetonide (fluonid, synalar); fluocinonide (lidex, topsyn); fluorometholone (oxylone); flurandrenolide (cordran); halcinonide (halog); medrysone (HMS liquiflim, medrocort); aclometasone dipropionate (aiclovate); betamethasone-17-berizoate (benisone, flurobate); betamethasone dipropionate (diprosone); betamethasone-17-valerate (valisone); clobetasol propionate (temovate); desonide (desowen, tridesilon); dexamethasone (aeroseb-D); desoximetasone (topicort); diflorasone diacetate (florone); flumethasone pivalate (locorten); fluocinolone acetonide (synalar, synalar-HP, neosynalar, fluonid); fluocinolone acetonide acetate (lidex; lidex-E; topsyn); fluorometholone (oxylone); flurandrenolide (cordran); halcinonide (halog); hydrocortisone (cort-dome, lubncort); hydrocortisone acetate (cortef, carmol HG, neo-cortef); hydrocortisone-17-valerate (westcort); prednisolone (metiderm); triarncinolone acetonide (kenalog, orabase, kenalog-S, mycolog, aristocort, aristocort-A, aristoderni, neo-aristoderm, neo-aristocort); temovate; diprolen; psorcon; temovate; diprolene; cyclocort; diprosone; florone; halog; lidex; maxiflor; topicort; aristocort A; diprosone; florone; maxiflor; valisone; cordran; kenalog; synalar; topicort LP; westcort; cordran; diprosone; kenalog; locold; synalar; valisone; westcort; aclovate; desowen; locorten; synalar; tridesilone; valisone; hydrocortisone; dexamethasone; flumethalone; prednisolone; methyiprednisolone; augmented betamethasone dipropionate (diprolene); diflorasone diacetate (psorcon); clobetasol propionate (temovate); halobetasol propionate (ultravate); anicinonide (cyclocort); betamethasone dipropionate (diprolene, diprosone); diflorasone diacetate (florone); halcinonide (halog); fluocinonide (lidex); diflorasone diacetate (maxiflor); betamethasone dipropionate (maxivate); diflorasone diacetate (psorcom); desoximetasone (topicort); (aristocort A); anicinonide (cyclocort); betamethasone dipropionate (diprosone); mometasone furoate (elocon); diflorasone diacetate (florone); halcinonide (halog); fluocinonide (lidex-E); diflorasone diacetate (maxiflor); betamethasone dipropionate (maxivate, psorion); betamethasone valerate (valisone); flurandrenolide (cordran); fluticasone propionate (cutivate); mometasone furoate (elocon); triaxncinolone acetonide (kenalog); fluocinolone acetonide (synalar); hydrocortisone valerate (westcort); flurandrenolide (cordran); fluticasone propionate (cutivate); betamethasone dipropionate (diprosone); triamcinolone acetonide (kenalog); hydrocortisone butyrate (locoid); fluocinolone acetonide (synalar); betamethasone valerate (valisone); hydrocortisone valerate (westcort); alclometasone dipropionate (aclovate); triamcinolone acetonide (aristocort); desonide (desowen); flumethasone pivalate (locorten); fluocinolone acetonide (synalar); desonide (tridesilon); betamethasone valerate (valisone); hydrocortisone (eldecort, dexamethasone, flumethalone, hydrocortisone, methylprednisolone, or prednisolone); betamethasone; and dexamethasone.

27. The adhesive patch of claim 25 wherein the corticosteroid is present up to about 5 wt. % of the therapeutic formulation.

28. The adhesive patch of claim 1 wherein the solvent comprises a polyhydric alcohol, water, or a combination thereof.

29. The adhesive patch of claim 28 wherein the polyhydric alcohol is propylene glycol, ethylene glycol, triethylene glycol, or a combination thereof.

30. The adhesive patch of claim 25 wherein the propylene glycol is present in about 3.0 wt. % to about 11.0 wt. % of the therapeutic formulation.

31. The adhesive patch of claim 28 wherein the water is present in about 2.0 wt. % to about 20.0 wt. % of the therapeutic formulation.

32. The adhesive patch of claim 29. wherein the triethylene glycol is present in about 2.0 wt. % to about 20.0 wt. % of the therapeutic formulation.

33. The adhesive patch of claim 1 wherein the solvent is present in about 3.0 wt % to about 25.0 wt. % of the therapeutic formulation.

34. The adhesive patch of claim 1 wherein the solvent comprises water; triethylene glycol; glycerin; propylene glycol; triacetin; 1,3-propane diol; 2-methyl-1,3-propane diol; glycerol ricinoleate; PEG-6 caprylic/capric glycerides; caprylic/capric triglycerides; propyleneglycol dicaprylate/dicaprate; glycerol monostearate; glycerol monocaprylate; glycerol monolaurate; neopentyl alcohol; 1-hexadecanol; hydroxypropyl beta-cyclodextrin; vitamin E; vitamin E acetate; deoxycholic acid; taurodeoxycholic acid; 3-[(3-cholamidopropyl) dimethylammonio]-1-propane-sulfonate; BigCHAP; cholic acid; cholesterol NF; propylene carbonate; lecithin; a pharmaceutically acceptable salt thereof; or a combination thereof.

35. The adhesive patch of claim 1 wherein the therapeutic formulation further comprises a filler.

36. The adhesive patch of claim 35 wherein the filler is malto dextrin.

37. The adhesive patch of claim 36 wherein the malto dextrin is present in about 1.0 wt. % to about 10.0 wt. % of the therapeutic formulation.

38. The adhesive patch of claim 1 wherein the pressure sensitive adhesive comprises one or more acrylic ester copolymers.

39. The adhesive patch of claim 38 wherein each of the one or more acrylic ester copolymers is present up to about 20.0 wt. % of the therapeutic formulation.

40. The adhesive patch of claim 38 wherein all of the one or more acrylic ester copolymers, combined, are present in about 5.0 wt. % to about 30.0 wt. % of the therapeutic formulation.

41. The adhesive patch of claim 1 wherein the pressure sensitive adhesive is located on the entire surface of the front side of the backing.

42. The adhesive patch of claim 1 wherein the pressure sensitive adhesive is at least partially embedded in the front side of the backing.

43. The patch of claim 1 wherein the pressure sensitive adhesive is completely embedded in the backing.

44. The adhesive patch of claim 1 wherein the pressure sensitive adhesive further comprises glycerin.

45. The adhesive patch of claim 44 wherein the glycerin is present in about 25.0 wt. % to about 70.0 wt. % of the therapeutic formulation.

46. The adhesive patch of claim 44 wherein the glycerin is present in about 40.0 wt. % to about 55.0 wt. % of the therapeutic formulation.

47. The adhesive patch of claim 1 wherein the pressure sensitive adhesive further comprises an emulsifier.

48. The adhesive patch of claim 47 wherein the emulsifier is pectin.

49. The adhesive patch of claim 48 wherein the pectin is present in about 2.0 wt. % to about 10.0 wt. % of the therapeutic formulation.

50. The adhesive patch of claim 1 wherein the therapeutic formulation further comprises a compound that provides structure and strength to the pressure sensitive adhesive or to the therapeutic formulation.

51. The adhesive patch of claim 50 wherein the compound that provides structure and strength to the pressure sensitive adhesive or to the therapeutic formulation is karaya, a polyacrylamide, xanthum gum, guar gum, a natural polymer, a synthetic polymer, a hydrophilic polymer, a hydrocolloidal polymer, starch, a starch derivative, vinyl acetate copolymer, polyvinyl pyrrolidone, polyethylene oxide, algin, derivatives of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS, or a mixture thereof.

52. The adhesive patch of claim 50 wherein the compound that provides structure and strength to the pressure sensitive adhesive or provides structure and strength to the therapeutic formulation is polyacrylamide.

53. The adhesive patch of claim 52 wherein the polyacrylamide is present in about 8.0 wt. % to about 30.0 wt. % of the therapeutic formulation.

54. The adhesive patch of claim 50 wherein the compound that provides structure and strength to the pressure sensitive adhesive or provides structure and strength to the therapeutic formulation is karaya.

55. The adhesive patch of claim 54 wherein the karaya is present in about 8.0 wt. % to about 40.0 wt. % of the therapeutic formulation.

56. The adhesive patch of claim 50 wherein the compound that provides structure and strength to the pressure sensitive adhesive or provides structure and strength to the therapeutic formulation is a combination of polyacrylamide and karaya.

57. The adhesive patch of claim 1 wherein the therapeutic formulation further comprises one or more skin conditioners.

58. The adhesive patch of claim 57 wherein the skin conditioner is calamine, aloe, lanolin, glycerin, Vitamin E, Vitamin E acetate, farnesol, glycyrrhetinic acid, or a combination thereof.

59. The adhesive patch of claim 58 wherein the aloe is present up to about 2.0 wt. % of the therapeutic formulation.

60. The adhesive patch of claim 58 wherein the Vitamin E acetate is present up to about 2.0 wt. % of the therapeutic formulation.

61. The adhesive patch of claim 1 wherein the therapeutic formulation further comprises one or more antimicrobial agents.

62. The adhesive patch of claim 61 wherein the antimicrobial agent is a β-lactam compound, an aminoglycoside, or an antifungal agent.

63. The adhesive patch of claim 61 wherein the antimicrobial agent is erythromycin, tetracycline, clindamycin, cephalosporin, or a combination thereof.

64. The adhesive patch of claim 1 wherein the therapeutic formulation further comprises one or more antiseptic agents.

65. The adhesive patch of claim 64 wherein the antiseptic agent is triclosan, phenoxy isopropanol, chlorhexidine gluconate, povidone iodine, or a combination thereof.

66. The adhesive patch of claim 1 wherein the therapeutic formulation further comprises one or more preservatives.

67. The adhesive patch of claim 66 wherein the preservative is quat-15, methyl paraben, ascorbic acid, or a combination thereof.

68. The adhesive patch of claim 66 wherein the preservative is present up to about 1.5 wt. % of the therapeutic formulation.

69. The adhesive patch of claim 1 having a thickness of about 0.20 mm to about 0.75 mm.

70. The adhesive patch of claim 1 further comprising a release liner that is mounted on the front side of the backing.

71. The adhesive patch of claim 70 wherein more than one patch is mounted on the release liner.

72. The adhesive patch of claim 71 wherein about 2 to about 20 adhesive patches are mounted on the release liner.

73. The adhesive patch of claim 1 that is crescent, circular, or oval.

74. The adhesive patch of claim 73 wherein the circular adhesive patch has a diameter of about 0.1 inch to about 1.0 inch.

75. The adhesive patch of claim 1 wherein the therapeutic formulation further comprises a complexing agent that effectively solubilizes or stabilizes the medicament.

76. The adhesive patch of claim 75 wherein the complexing agent is a cyclodextrin, or a derivative of cyclodextrin.

77. The adhesive patch of claim 76 wherein the cyclodextrin or the derivative of cyclodextrin is alpha-cyclodextrin, beta-cyclodextrin, gamma-cyclodextrin, alpha-cyclodextrin sulfate, beta-cyclodextrin, sulfate, gamma-cyclodextrin sulfate, alpha-hydroxypropyl cyclodextrin, beta-hydroxypropyl cyclodextrin, gamma-hydroxypropyl cyclodextrin, alpha-cyclodextrin phosphate, beta-cyclodextrin phosphate, or gamma-cyclodextrin phosphate.

78. An adhesive patch comprising a flexible backing having a front side and a back side and a therapeutic formulation positioned on at least a portion of the front side of the backing, in at least a portion of the front side of the backing, or on and in at least a portion of the front side of the backing; wherein at least a portion of the backing is treated with a sizing agent such that the portion of the backing treated with the sizing agent has a surface energy of about 20 dynes/cm$^2$ to about 65 dynes/cm$^2$; wherein the therapeutic formulation comprises:

a corticosteroid;

a cyclodextrin or a derivative of cyclodextrin that effectively solubilizes the corticosteroid; and a pressure sensitive adhesive.

79. An adhesive patch comprising a flexible backing having a front side and a back side and a therapeutic formulation positioned on and in at least a portion of the front side of the backing such that the therapeutic formulation is partially embedded in at least a portion of the front side of the backing; wherein at least a portion of the backing is treated with a sizing agent such that the portion of the backing treated with the sizing agent has a surface energy of about 20 dynes/cm$^2$ to about 65 dynes/cm$^2$; wherein the therapeutic formulation comprises:

salicylic acid or a pharmaceutically acceptable salt thereof present in about 0.5 wt. % to about 2.0 wt. % of the therapeutic formulation;

a solvent that dissolves the salicylic acid; and a pressure sensitive adhesive.

80. An adhesive patch comprising a flexible backing having a front side and a back side and a therapeutic formulation positioned on at least a portion of the front side of the backing, in at least a portion of the front side of the backing, or on and in at least a portion of the front side of the backing; wherein at least a portion of the backing is treated with a sizing agent such that the portion of the backing that is treated with the sizing agent has a surface energy of about 20 dynes/cm$^2$ to about 65 dynes/cm$^2$; wherein the therapeutic formulation comprises:

a medicament selected from one or more topical psoriasis drugs, one or more topical dermatitis drugs, one or more topical eczema drugs, or a combination thereof; and a hot melt adhesive.

81. A method for treating at least one of psoriasis, dermatitis, and eczema in a mammal in need thereof comprising applying to the skin surface of the mammal having the psoriasis, dermatitis, or eczema an adhesive patch of any one of claim 1, 78, 79 or 80 for a period of time effective to treat psoriasis, dermatitis, or eczema.

82. The method of claim 81 wherein the mammal is a human.

83. The method of claim 81 wherein the skin surface of the mammal having the psoriasis, dermatitis, or eczema is the head, face, scalp, neck, shoulder, chest, back, arm, hand, leg, foot, navel, breast, underarm, groin, buttock, elbow, knee, eyelid, outer surface of the ear, gluteal fold, or any combination thereof.

84. The method of claim 81 wherein the period of time is about one hour to about twelve hours.

85. A method for exfoliating the skin surface of a mammal comprising applying to the skin surface of the mammal in need of such exfoliation an adhesive patch of any one of claim 1, 78, 79 or 80 and removing the adhesive patch, thereby effectively exfoliating the skin surface.

86. The method of claim 85 wherein the mammal is a human.

87. The method of claim 85 wherein the adhesive patch is applied to the skin surface of the mammal for about one second to about 12 hours.

88. The method of claim 85 wherein the skin surface in need of such exfoliation is the head, face, scalp, neck, shoulder, chest, back, arm, hand, leg, foot, navel, breast, underarm, groin, buttock, elbow, knee, eyelid, outer surface of the ear, gluteal fold, or any combination thereof.

* * * * *